United States Patent
Cameron et al.

(10) Patent No.: US 6,756,388 B1
(45) Date of Patent: Jun. 29, 2004

(54) BENZOTHIOPHENES AND RELATED COMPOUNDS AS ESTROGEN AGONISTS

(75) Inventors: Kimberly O. Cameron, East Lyme, CT (US); Paul Da Silva-Jardine, Mystic, CT (US); Eric R. Larson, Mystic, CT (US); James R. Hauske, Marlboro, MA (US); Robert L. Rosati, Stonington, CT (US)

(73) Assignee: Pfizer Inc., New York, NY (US)

( * ) Notice: Subject to any disclaimer, the term of this patent is extended or adjusted under 35 U.S.C. 154(b) by 1826 days.

(21) Appl. No.: 08/628,605

(22) PCT Filed: Sep. 13, 1994

(86) PCT No.: PCT/IB94/00282
§ 371 (c)(1),
(2), (4) Date: Jul. 1, 1996

(87) PCT Pub. No.: WO95/10513
PCT Pub. Date: Apr. 20, 1995

Related U.S. Application Data

(63) Continuation of application No. 08/135,386, filed on Oct. 12, 1993.

(51) Int. Cl.[7] .................. A61K 31/445; C07D 409/06
(52) U.S. Cl. .................................. 514/324; 546/202
(58) Field of Search ................. 514/212, 227, 514/255, 319, 320, 324, 337, 422, 443; 540/596, 609; 544/106, 153; 546/196, 202, 205, 209, 274, 340, 342, 201; 548/525, 527, 528, 543, 550, 551, 560, 570, 571, 576; 564/323, 324; 549/49, 467, 469, 470, 471

(56) References Cited

U.S. PATENT DOCUMENTS 4,133,814 A * 1/1979 Jones et al. .............. 546/202
4,418,068 A * 11/1983 Jones et al. .............. 546/202
5,223,510 A * 6/1993 Gubin et al. .............. 514/299

FOREIGN PATENT DOCUMENTS

EP 516257 * 12/1992
WO WP 93/10113 * 5/1993

* cited by examiner

Primary Examiner—Ceila Chang
(74) Attorney, Agent, or Firm—Peter C. Richardson; Gregg C. Benson; Todd M. Crissey

(57) ABSTRACT

The invention is a compound of Formula (I):

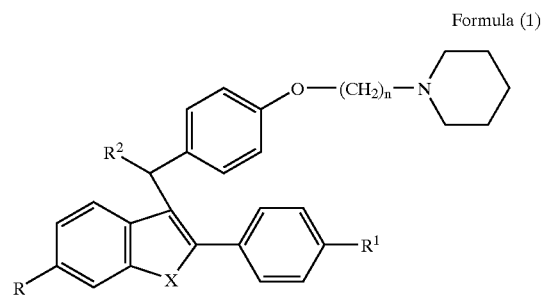

Formula (1)

wherein
R is —OH,
$R^1$ is —OH,
$R^2$ is —H,
n is 2 or 3 and
X is sulfur, or
a pharmaceutically acceptable salt of a compound having Formula (1), or
a pharmaceutical composition comprising a compound having Formula (1) or a pharmaceutically acceptable salt thereof, or
methods of treating bone loss, breast cancer or prostate cancer comprising administering an effective amount of the compound having Formula (I) or a pharmaceutically acceptable salt thereof.

3 Claims, No Drawings

BENZOTHIOPHENES AND RELATED COMPOUNDS AS ESTROGEN AGONISTS

This application is a 35 U.S.C. 371 of International Application No. PCT/IB94/00282, filed on Sep. 19, 1994, which is a continuation of U.S. patent application Ser. No. 08/135,386, filed on Oct. 12, 1993.

BACKGROUND OF THE INVENTION

The value of naturally occurring estrogens and synthetic compositions demonstrating "estrogenic" activity has been in their medical and therapeutic uses. A traditional listing of the therapeutic applications for estrogens alone or in combination with other active agents includes: oral contraception; relief for the symptoms of menopause; prevention of threatened or habitual abortion; relief of dysmenorrhea; relief of dysfunctional uterine bleeding; an aid in ovarian development; treatment of acne; diminution of excessive growth of body hair in women (hirsutism); the prevention of cardiovascular disease; treatment of osteoporosis; treatment of prostatic carcinoma; and suppression of post-partum lactation [Goodman and Gilman, The Pharmacological Basis Of Therapeutics (Seventh Edition) Macmillan Publishing Company, 1985, pages 1421–1423]. Accordingly, there has been increasing interest in finding newly synthesized compositions and new uses for previously known compounds which are demonstrably estrogenic, this is, able to mimic the action of estrogen in estrogen responsive tissue.

From the viewpoint of pharmacologists interested in developing new drugs useful for the treatment of human diseases and specific pathological conditions, it is most important to procure compounds with some demonstrable estrogen-like function but which are devoid of proliferative side-effects. Exemplifying this latter view, osteoporosis, a disease in which bone becomes increasingly more fragile, is greatly ameliorated by the use of fully active estrogens; however, due to the recognized increased risk of uterine cancer in patients chronically treated with active estrogens, it is not clinically advisable to treat osteoporosis in intact women with fully active estrogens for prolonged periods. Accordingly estrogen agonists are the primary interest and focus.

Osteoporosis is a systemic skeletal disease, characterized by low bone mass and deterioration of bone tissue, with a consequent increase in bone fragility and susceptibility to fracture. In the U.S., the condition affects more that 25 million people and causes more than 1.3 million fractures each year, including 500,000 spine, 250,000 hip and 240,000 wrist fractures annually. These cost the nation over $10 billion. Hip fractures are the most serious, with 5–20% of patients dying within one year, and over 50% of survivors being incapacitated.

The elderly are at greatest risk of osteoporosis, and the problem is therefore predicted to increase significantly with the aging of the population. Worldwide fracture incidence is forecast to increase three-fold over the next 60 years, and one study estimates that there will be 4.5 million hip fractures worldwide in 2050. Women are at greater risk of osteoporosis than men. Women experience a sharp acceleration of bone loss during the five years following menopause. Other factors that increase the risk include smoking, alcohol abuse, a sedentary lifestyle and low calcium intake.

Estrogen is the agent of choice in preventing osteoporosis or post menopausal bone loss in women; it is the only treatment which unequivocally reduces fractures. However, estrogen stimulates the uterus and is associated with an increased risk of endometrial cancer. Although the risk of endometrial cancer is thought to be reduced by a concurrent use of a progestogen, there is still concern about possible increased risk of breast cancer with the use of estrogen.

There is a need for improved estrogen agonists which exert selective effects on different tissues in the body. Tamoxifen, 1-(4-β-dimethylaminoethoxyphenyl)-1,2-diphenyl-but-1-ene, is an antiestrogen which has a palliative effect on breast cancer, but is reported to have estrogenic activity in the uterus.

Recently it has been reported (Osteoporosis Conference Scrip No. 1812/13 Apr. 16/20, 1993, p29) that raloxifene, 6-hydroxy-2-(4-hydroxyphenyl)-3-[4-(2-piperidinoethoxy)benzoyl]benzo[b]thiophene, mimics the favorable action of estrogen on bone and lipids but, unlike estrogen, has minimal uterine stimulatory effect. (Breast Cancer Res. Treat. 10(1). 1987 p 31–36 Jordan, V.C. et al.)

Raloxifene as well as ethers and esters thereof and related compounds are described as antiestrogen and antiandrogenic materials which are effective in the treatment of certain mammary and prostate cancers. See U.S. Pat. No. 4,418,068 and Charles D. Jones, et al., J. Med. Chem. 1984, 27, 1057–1066.

Jones, et al in U.S. Pat. No. 4,133,814 describe derivatives of 2-phenyl-3-aroylbenzothiophene and 2-phenyl-3-aroylbenzothiophene-1-oxides which are useful as antifertility agents as well as suppressing the growth of mammary tumors.

Related 2-phenyl-3-aroylbenzothiophenes have also been claimed to modulate the clearance of antibody coated cells from the circulation of mammals, thus providing a method of treating autoimmune disease, U.S. Patent No. 5,075,321.

SUMMARY OF INVENTION

This invention provides compounds of the formula

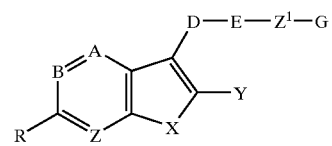

(1)

wherein

A, B and Z are independently
  (a) —CH=,
  (b) —CR$^4$=,
  (c) =N—;

X is
  (a) —S—,
  (b) —O—,
  (c) —NH—,
  (d) —NR$^2$—,
  (e) —CH$_2$CH$_2$—,
  (f) —CH$_2$CH$_2$CH$_2$—,
  (g) —CH$_2$O—,
  (h) —OCH$_2$—,
  (i) —CH$_2$S—,
  (j)

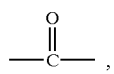

(k) —SCH$_2$—,
  (l) —N=CR$^2$—,
  (m) —R$^2$C=N—;

Y is
(a) phenyl, optionally substituted with 1–3 substituents independently selected from the group consisting of halo, hydroxy, $C_1$–$C_4$ alkyl, $C_1$–$C_4$ alkoxy,

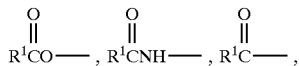

and $R^1SO_2NH$—;
(b) $C_1$–$C_8$ alkyl, said alkyl groups being optionally substituted with 1–3 substituents independently selected from the group consisting of

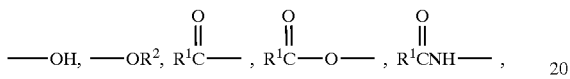

and $R^1SO_2NH$—;
(c) $C_3$–$C_8$ cycloalkyl, optionally substituted with 1–2 substituents independently selected from the group consisting of —OH,—$R^1$,

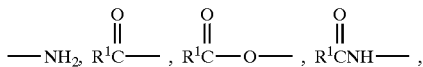

and $R^1SO_2NH$—;
(d) $C_3$–$C_8$ cycloalkenyl, optionally substituted with 1–2 substituents independently selected from the group consisting of —OH,

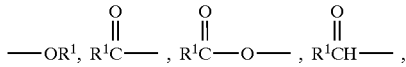

and $R^1SO_2NH$—;
(e) a five membered heterocycle containing up to two heteroatoms selected from the group consisting of —O—, —$NR^2$— and —S(O)$_n$—, optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, aryl ($C_1$–$C_4$)alkyl,—$CO_2H$, —CN, —CONHOR$^1$, —$SO_2NHR^1$, —$NH_2$, $C_1$–$C_4$ alkylamino, $C_1$–$C_4$ dialkylamino, —$NHSO_2R^1$,—NHCOR$^1$, —$NO_2$, and -aryl;
a six membered heterocycle containing up to two heteroatoms selected from the group consisting of —O—, —$NR^2$— and —S(O)$_n$— optionally substituted with 1–3 substituents independently selected from the group consisting of hydrogen, hydroxyl, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, aryl ($C_1$–$C_4$)alkyl,—$CO_2H$, —CN, —CONHOR$^1$, —$SO_2NHR^1$, —$NH_2$, $C_1$–$C_4$ alkylamino, $C_1$–$C_4$ dialkylamino, —$NHSO_2R^1$,—NHCOR$^1$, —$NO_2$, and -aryl;
(g) a bicyclic ring system consisting of a five or six membered heterocyclic ring fused to a phenyl ring, said heterocyclic ring containing up to two heteroatoms selected from the group consisting of —O—, —$NR^2$— and —S(O)$_n$—, optionally substituted with 1–3 substituents independently selected from the group consisting of hydrogen, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, aryl ($C_1$–$C_4$)alkyl,—$CO_2H$, —CN, —CONHOR$^1$, —$SO_2NHR^1$, —$NH_2$, $C_1$–$C_4$ alkylamino, $C_1$–$C_4$ dialkylamino, —$NHSO_2R^1$, —NHCOR$^1$, —$NO_2$, —OH, and -aryl;

D is
(a) —CO—,
(b) —$CR^2R^3$—,
(c) —CONH—,
(d) —NHCO—,
(e) —$CR^2$(OH)—,
(f) —$CONR^2$—,
(g) —$NR^2CO$—,
(h)

(i)

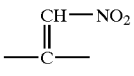

(j)

E is
(a) a single bond;
(b) phenyl, or phenyl substituted with up to three substituents independently selected from the group consisting of hydrogen, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$)alkyl, aryl ($C_1$–$C_4$)alkyl,—$CO_2H$, —CN,—CONHOR, —$SO_2NHR$, —$NH_2$, $C_1$–$C_4$ alkylamino, $C_1$–$C_4$ dialkylamino, —$NHSO_2R$, —NHCOR$^1$,—$NO_2$, and -aryl; or
(c) a 5 or 6 membered heterocycle, optionally fused to a phenyl ring containing up to two heteroatoms selected from the group consisting of —O—, —$NR^2$— and —S(O)$_n$— optionally substituted with 1–3 substituents independently selected from the group consisting of hydrogen, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) alkyl, aryl ($C_1$–$C_4$) alkyl, —$CO_2H$, —CN,—CONHOR, —$SO_2NHR$, —$NH_2$, $C_1$–$C_4$ alkylamino, $C_1$–$C_4$ dialkylamino, —$NHSO_2R$,—NHCOR$^1$, —$NO_2$, and -aryl;

$Z^1$ is
(a) —(CH$_2$)$_p$ W(CH$_2$)$_q$—,
(b) —O(CH$_2$)$_p$ CR$^5$ R$^6$—,
(c) —O(CH$_2$)$_p$W(CH$_2$)$_q$;

G is
(a) —NR⁷R⁸,
(b)

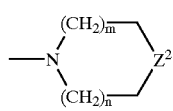

wherein n is 0, 1 or 2; m is 1, 2 or 3; Z² is —NH—, —O—, —S—, or —CH₂—; optionally fused on adjacent carbon atoms with one or two phenyl rings and, optionally independently substituted on carbon with one to three substituents and, optionally, independently on nitrogen with a chemically suitable substituent selected from

—OR¹, (1)

—SO₂NR²R³, (2)

 (3)

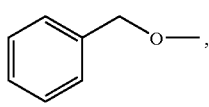 (4)

halogen, (5)

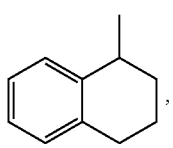 (6)

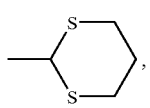 (7)

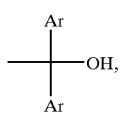 (8)

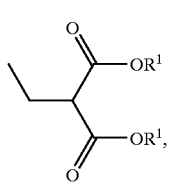 (9)

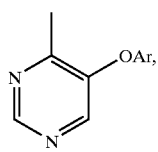 (10)

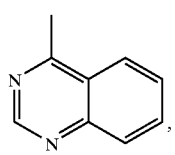 (11)

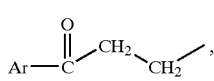

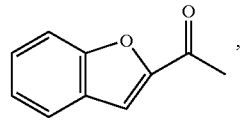 (12)

—C≡CR¹, (13)

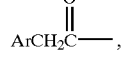 (14)

ArCH₂C—, (15)

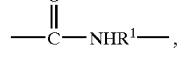

—C—NHR¹—, (16)

—CR¹, (17)

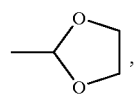 (18)

Ar—CH₂—, (19)

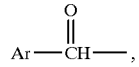 (20)

Ar—CH—,

—C—OR¹, (21)

—(CF₂)ₘCF₃, (22)

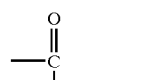

(c)

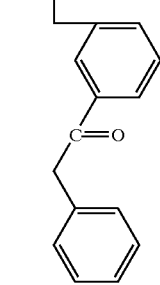

(d)

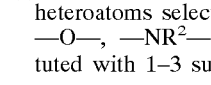

(e) a 5 or 6 membered heterocycle containing up to two heteroatoms selected from the group consisting of —O—, —NR²— and —S(O)ₙ—optionally substituted with 1–3 substituents independently selected from the group consisting of hydrogen, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) alkyl, aryl ($C_1$–$C_4$)alkyl, —$CO_2H$, —CN, —CONHOR, —$SO_2NHR$, —$NH_2$, $C_1$–$C_4$ alkylamino, $C_1$–$C_4$ dialkylamino, —$NHSO_2R$,—$NHCOR^1$, —$NO_2$, and -aryl; said heterocycle being joined to group $Z^1$ by a carbon to carbon bond or carbon-nitrogen bond;

(f) a bicyclic amine containing a five to twelve carbon atoms, either bridged or fused and optionally substituted with 1–3 substituents independently selected from the group consisting of hydrogen, halo, $C_1$–$C_4$ alkyl, trihalomethyl, $C_1$–$C_4$ alkoxy, trihalomethoxy, $C_1$–$C_4$ acyloxy, $C_1$–$C_4$ alkylthio, $C_1$–$C_4$ alkylsulfinyl, $C_1$–$C_4$ alkylsulfonyl, hydroxy ($C_1$–$C_4$) alkyl, aryl ($C_1$–$C_4$)alkyl, —$CO_2H$, —CN, —CONHOR, —$SO_2NHR$, —$NH_2$, $C_1$–$C_4$ alkylamino, $C_1$–$C_4$ dialkylamino, —$NHSO_2R$,—$NHCOR^1$, —$NO_2$, and -aryl;

$Z^1$ and G in combination may be

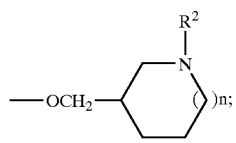

Ar is phenyl or naphthyl optionally substituted with up to three substituents independently selected from $R^4$;

W is
(a) —$CH_2$—,
(b) —CH═CH—,
(c) —O—,
(d) —$NR^2$—,
(e) —S(O)$_n$—, (f)

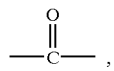

(g) —$CR^2(OH)$—,
(h) —$CONR^2$—,
(i) —$NR^2CO$—,
(j)

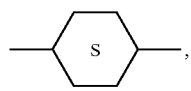

(k) —C≡C—;

R is
(a) halogen,
(b) —$NR^3R^2$,
(c) —$NHCOR^2$,
(d) —$NHSO_2R^2$,
(e) —$CR^2R^3OH$,
(f) —$CONR^2R^3$,
(g) —$SO_2NR^2R^3$,
(h) hydroxyl,
(i) $R^1O$—, (j)

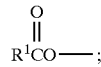

$R^1$ is $C_1$–$C_6$ alkyl or phenyl optionally substituted with up to three substituents independently selected from $C_1$–$C_6$ alkyl, halogen, alkoxy, hydroxy and carboxy;

$R^2$ and $R^3$ are independently
(a) hydrogen,
(b) $C_1$–$C_4$ alkyl;

$R^4$ is
(a) hydrogen,
(b) halogen,
(c) $C_1$–$C_4$ alkyl,
(d) $C_1$–$C_4$ alkoxy,
(e) $C_1$–$C_4$ acyloxy,
(f) $C_1$–$C_4$ alkylthio,
(g) $C_1$–$C_4$ alkylsulfinyl,
(h) $C_1$–$C_4$ alkylsulfonyl,
(i) hydroxy ($C_1$–$C_4$)alkyl,
(j) aryl ($C_1$–$C_4$)alkyl,
(k) —$CO_2H$,
(l) —CN,
(m) —CONHOR,
(n) —$SO_2NHR$,
(o) —$NH_2$,
(p) $C_1$–$C_4$ alkylamino,
(q) $C_1$–$C_4$ dialkylamino,
(r) —$NHSO_2R$,
(s) —$NO_2$,
(t) -aryl;

$R^5$ and $R^6$ are independently $C_1$–$C_8$ alkyl or together form a $C_3$–$C_{10}$ carbocyclic ring;

$R^7$ and $R^8$ are independently
(a) phenyl,
(b) a $C_3$–$C_{10}$ carbocyclic ring, saturated or unsaturated,
(c) a $C_3$–$C_{10}$ heterocyclic ring containing up to two heteroatoms, selected from —O—, —N— and —S—
(d) H,
(e) $C_1$–$C_6$ alkyl,
(f) or form a 3 to 8 membered nitrogen containing ring with $R^5$ or $R^6$;

$R^7$ and $R^8$ in either linear or ring form may optionally be substituted with up to three substituents independently selected from $C_1$–$C_6$ alkyl, halogen, alkoxy, hydroxy and carboxy;

a ring formed by $R^7$ and $R^8$ may be optionally fused to a phenyl ring;

m is 1, 2 or 3;
n is 0, 1 or 2;
p is 0, 1, 2 or 3;
q is 0, 1, 2, or 3;

and geometric and optical isomers, pharmaceutically acceptable esters, ethers and salts thereof;

with the proviso that when A, B and Z are each —CH═, Y is 4-hydroxy phenyl, X is sulfur, D is —CO—, E is 1,4-disubstituted phenyl, R is —OH, and $Z^1$ is —$OCH_2CH_2$— then G must be a group other than

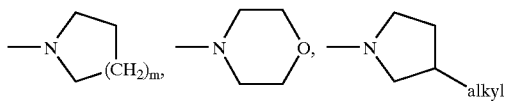

or —N—($C_1$–$C_4$ alkyl)$_2$; and with the further proviso that if R is

G must be a group other than

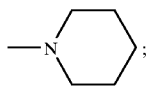

and with the further proviso that when A, B and Z are each —CH=, X is S, Y is cycloalkyl or cycloalkenyl;

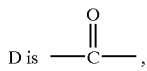

E is 1,4 disubstituted phenyl; and $Z^1$ is methylene, $O(CH_2)_m$—, ethylene or propylene; G must be other than

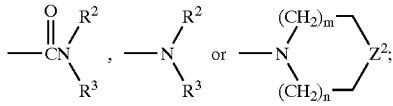

and with the further proviso that when D is —$CR^2R^3$— and W is —CO— or —$S(O)_n$—; G must be other than:
a) —$NR^{11}R^{12}$ where $R^{11}$ and $R^{12}$ are separately hydrogen, alkyl, alkenyl, cycloalkyl, haloalkyl, aryl or arylalkyl;

b) 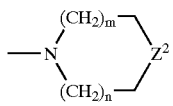

where n is 0, 1 or 2; m is 1, 2 or 3; and $Z^2$ is —NH—, O—, —S— or —$CH_2$—;
and with the further proviso that when A, B and Z are each —CH=, Y is 4-hydroxyphenyl, X is —$CH_2$—$CH_2$— or —CH=CH—; D is CO, E is 1,4-disubstituted phenyl, and $Z^1$ is —$OCH_2CH_2$—; then G must be a group other than

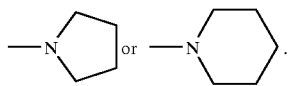

This invention provides preferred groups of compounds of formula 1 wherein

1. R is —OH;
2. A, B and Z are independently selected from —CH= and —CF=;
3. X is —S—;
4. D is —CO— or $CH_2$—;
5. E is 1,4-linked phenyl, pyridyl, pyrimidine,

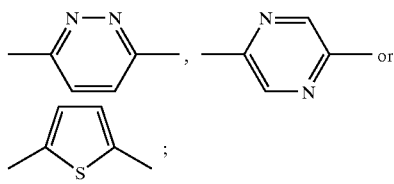

6. $Z^1$ is —$OCH_2CH_2$—, —$CH_2CH_2$—, —$CH_2$—,

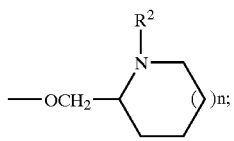

7. G is

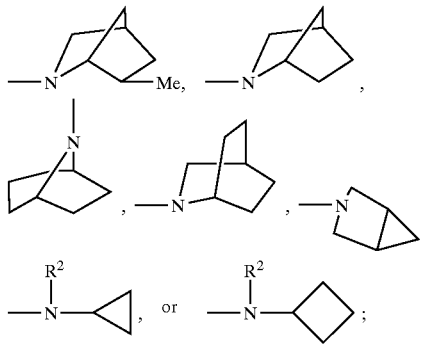

8. R is —OH; A, B and Z are —CH—; X is S; Y is

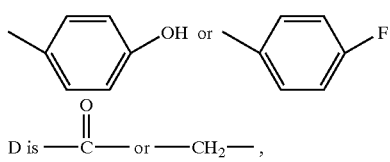

E is 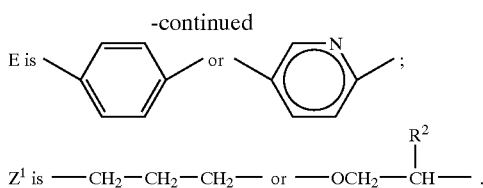

$Z^1$ is 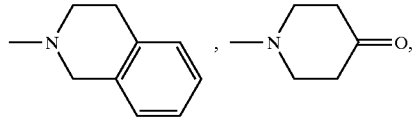.

A further preferred group of compounds are those of formula 1 wherein:

A, B and Z are —CH=;
X is —S—;
Y is phenyl, 4-hydroxyphenyl, 4-chlorophenyl, 4-fluorophenyl,

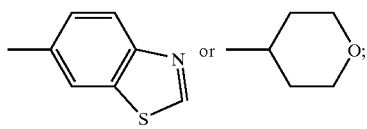

R is —OH—;
D is —CO— or —CH$_2$—;
E is phenyl or pyridyl; and
$Z^1$ is —OCH$_2$CH$_2$—, —C≡C—CH$_2$—, —OCH$_2$—, or —NHCH$_2$CH$_2$—.

Further preferred with the above group are those compounds wherein:

G is 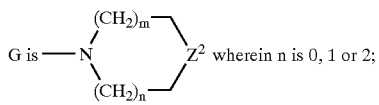 wherein n is 0, 1 or 2;

m is 1, 2 or 3 and $Z^2$ is —NH—, —O—, —S— or —CH$_2$—.

Or those compounds wherein G is:

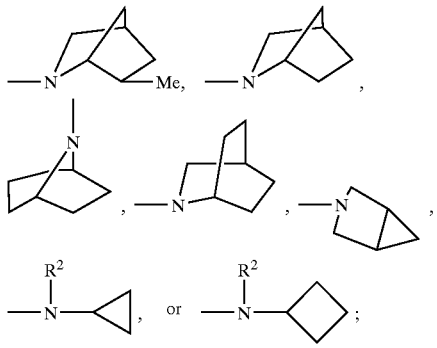

Or those compounds wherein G is:

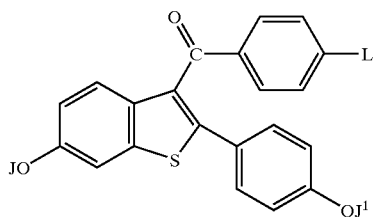

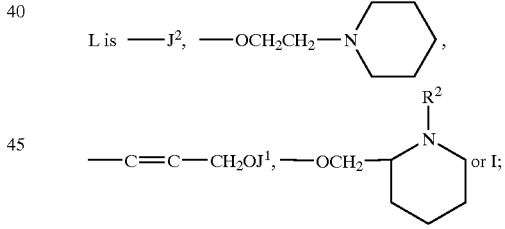

In another aspect this invention provides intermediate compounds of the formula

[structure]

wherein:
J, $J^1$ and $J^2$ are independently —H, —CH$_3$, —SO$_2$CH$_3$ or —SO$_2$CF$_3$; and L is —$J^2$, —OCH$_2$CH$_2$—N[piperidine], —C≡C—CH$_2$OJ$^1$, —OCH$_2$—[piperidine with NR$^2$] or I;

with the proviso that only two of J, $J^1$ and $J^2$ may be —H.

In yet another aspect this invention provides a method of treating bone loss associated with estrogen deficiency in a mammal which comprises administering to a mammal in need of such treatment an amount of a compound of claim 1 which is effective in treating said bone loss.

In yet another aspect this invention provides pharmaceutical composition comprising an amount of compound of claim 1 which is effective in treating estrogen deficiency bone loss in a mammal and a pharmaceutically inert carrier.

In yet another aspect this invention provides a method for the treatment or prevention of cardiovascular disease which comprises administering to a mammal in need of such treatment an amount of a compound of claim 1 which is effective in treating or preventing said cardiovascular disease.

In yet another aspect this invention provides a method of treating a mammal having a mammary tumor which comprises administering to said mammal a mammary tumor-inhibiting effective amount of a compound of claim 1.

In yet another aspect this invention provides a method for the treatment or prevention of diseases or syndromes which are caused by an estrogen deficient state in a mammal which comprises administering to a mammal in need of such treatment or prevention an amount of a compound of claim 1 which is effective in treating said disease or syndrome.

DETAILED DESCRIPTION OF THE INVENTION

In this document, all measurements are expressed in weight units, unless otherwise stated, except that ratios of solvents are expressed in volume units.

The general chemical terms used in the formulae above have their usual meanings. For example, the terms $C_1$–$C_{14}$ alkyl, and $C_1$–$C_4$ alkoxy include groups such as methyl, ethyl, isopropyl, butyl, s-butyl, tetradecyl, undecyl, neopentyl, 2,2-dimethylhexyl, 3-ethylnonyl, 3-butylheptyl, dodecyl, methoxy, propoxy and i-butoxy.

The terms $C_1$–$C_3$ chloroalkyl and $C_1$–$C_3$ fluoroalkyl include methyl, ethyl, propyl and isopropyl substituted to any desired degree with chlorine or fluorine atoms, from one atom to full substitution. The term $C_5$–$C_7$ cycloalkyl includes cyclopentyl, cyclohexyl and cycloheptyl.

Halo means chloro, bromo, iodo and fluoro. Aryl (Ar) includes phenyl and naphthyl optionally substituted with one to three substituents independently selected from $R^4$ as defined above. DTT means dithiothreitol. DMSO means dimethyl sulfoxide. EDTA means ethylene diamine tetra acetic acid.

Estrogen agonists are herein defined as chemical compounds capable of binding to the estrogen receptor sites in mammalian tissue, and mimic the actions of estrogen in one or more tissues.

One of ordinary skill will recognize that certain substituents listed in this invention will be chemically incompatible with one another or with the heteroatoms in the compounds, and will avoid these incompatibilties in selecting compounds of this invention.

The chemist of ordinary skill will recognize that certain compounds of this invention will contain atoms which may be in a particular optical or geometric configuration. All such isomers are included in this invention.

Likewise, the chemist will recognize that various pharmaceutically acceptable esters, ethers and salts may be prepared from certain compounds of this invention. All of such esters, ethers and salts are included in this invention.

The compounds of this invention are valuable estrogen agonists and pharmaceutical agents or intermediates thereto. Those which are estrogen agonists are useful for oral contraception; relief for the symptoms of menopause; prevention of threatened or habitual abortion; relief of dysmenorrhea; relief of dysfunctional uterine bleeding; an aid in ovarian development; treatment of acne; diminution of excessive growth of body hair in women (hirsutism); the prevention and treatment of cardiovascular disease; prevention and treatment of atherosclerosis; prevention and treatment of osteoporosis; treatment of prostatic carcinoma; and suppression of post-partum lactation. These agents also have a beneficial effect on plasma lipid levels.

While the compounds of this invention are estrogen agonists in bone, they are also antiestrogens in breast tissue and as such would be useful in the treatment and prevention of breast cancer.

Bone Mineral Density

Bone mineral density, a measure of bone mineral content, accounts for greater than 80% of a bone's strength. Loss of bone mineral density with age and/or disease reduces a bone's strength and renders it more prone to fracture. Bone mineral content is accurately measured in people and animals by dual x-ray absorptiometry (DEXA) such that changes as little as 1% can be quantified. We have utilized DEXA to evaluate changes in bone mineral density due to estrogen deficiency following ovariectomy (surgical removal of ovaries) and treatment with vehicle, estradiol (E2), keoxifen (raloxifen), or other estrogen agonists. The purpose of these studies was to evaluate the ability of the compounds of this invention to prevent estrogen deficiency bone loss as measured by DEXA.

Female (S-D) rats 4–6 months of age underwent bilateral ovariectomy or sham surgery and allowed to recover from anesthesia. Rats were s.c. injected with either 10 $\mu$g estradiol or 100 $\mu$g of compound daily for 28 days. All compounds were weighed and dissolved in 10% ethanol in sterile saline. After 28 days the rats were killed and femora removed and defleshed. The femoral were positioned on a Hologic QDR1000W (Hologic, Inc. Waltham, Mass.) and bone mineral density was determined in the distal portion of the femur at a site from 1 cm to 2 cm from the distal end of the femur using the high resolution software supplied by Hologic. Bone mineral density is determined by dividing the bone mineral content by the bone area of the distal femur. Each group contained at least 6 animals. Mean bone mineral density was obtained for each animal and statistical differences ($p<0.05$) from the vehicle-treated ovariectomy and sham-operated group were determined by t test.

In Vitro Estrogen Receptor Binding Assay

An in vitro estrogen receptor binding assay, which measures the ability of the compounds of the present invention to displace [3H]-estradiol from human estrogen receptor obtained by recombinant methods in yeast, was used to determine the estrogen receptor binding affinity of the compounds of this invention. The materials used in this assay were: (1) Assay buffer, TD-0.3 (containing 10 nM Tris, pH 7.6, 0.3 M potassium chloride and 5 mM DTT, pH 7.6); (2) The radioligand used was [3H]-estradiol obtained from New England Nuclear; (3) the cold ligand used was estradiol obtained from Sigma (4) recombinant human estrogen receptor, hER.

A solution of the compound being tested was made up in TD-0.3 with 4% DMSO and 16% ethanol. The tritiated estradiol was dissolved in TD-0.3 such that the final concentration in the assay was 5nM. The hER was also diluted with TD-0.3 such that 4–10 $\mu$g of total protein was in each assay well. Using microtitre plates, each incubate received 50 ul of cold estradiol (nonspecific binding) or the compound solution, 20 uL of the tritiated estradiol and 30 ul of hER solutions. Each plate contained in triplicate total binding and varying concentrations of the compound. The plates were incubated overnight at 4° C. The binding reaction was then terminated by the addition and mixing of 100 mL of 3% hydroxylapatite in 10 mM tris, pH 7.6 and incubation for 15 minutes at 4° C. The mixtures was centrifuged and the pellet washed four times with 1% Triton-X100 in 10 mM Tris, pH 7.6. The hydroxylapatite pellets were suspended in Ecoscint A and radioactivity was assessed using beta scintigraphy. The mean of all triplicate data points (counts per minute, cpm's) as determined. Specific binding was calculated by subtracting nonspecific cpm's (defined as counts that remain following separation of reaction mixture containing recombinant receptor, radioligand, and excess unlabeled ligand)

from total bound cpm's (defined as counts that remain following the separation of reaction mixture containing only recombinant receptor, radioligand). Compound potency was determined by means of IC50 determinations (the concentration of a compound needed to inhibition 50% of the of the total specific tritiated estradiol bound). Specific binding in the presence of varying concentrations of compound was determined and calculated as percent specific binding of total specific radioligand bound. Data were plotted as percent inhibition by compound (linear scale) versus compound concentration (log scale). Compounds of the present invention were found to have IC50 values at or less than 20 pM.

Effect on Total Cholesterol Levels

The effect of the compounds of the present invention on plasma levels of total cholesterol was measured in the following way. Blood samples were collected via cardiac puncture from anesthetized female (S-D) rats 4–6 months of age that were bilaterally ovariectomized and treated with the compound (100 µg/day sc for 28 days or with vehicle for the same time), or sham operated. The blood was placed in a tube containing 30 µL of 5% EDTA (10 µL EDTA/1 mL of blood). After centrifugation at 2500 rpm for 10 minutes at 20° C. the plasma was removed and stored at −20° C. unit assay. The total cholesterol was assayed using a standard enzymatic determination kit from Sigma Diagnostics (Procedure No. 352). Preferred compounds of the invention include:

[6-Hydroxy-2-(4-hydroxy-phenyl)-benzo[b]thiophen-3-yl]-{4-[2-(4-methyl-piperazin-1-yl)-ethoxy]-phenyl}-methanone;

1-(2-{4-[6-Hydroxy-2-(4-hydroxy-phenyl)-benzo[b]thiophene-3-carbonyl]-phenoxy}-ethyl)-piperidin-4-one;

{4-[2-(Bicyclo[2.2.1]hept-2-ylamino)-ethoxy]-phenyl}-[6-hydroxy-2-(4-hydroxy-phenyl)-benzo[b]thiophen-3-yl]-methanone;

[6-Hydroxy-2-(4-hydroxy-phenyl)-benzo[b]thiophen-3-yl]-{4-[2-(6-methyl-2-aza-bicyclo[2.2.1]hept-2-yl)-ethoxy]-phenyl}-methanone;

[4-(2-Cyclopropylamino-ethoxy)-phenyl]-[6-hydroxy-2-(4-hydroxy-phenyl)-benzo[b]thiophen-3-yl]-methanone;

{4-[2-(2-Aza-bicyclo[2.2.1]hept-2-yl)-ethoxy]-phenyl}-[6-hydroxy-2-(4hydroxy-phenyl)-benzo[b]thiophen-3-yl]-methanone;

[6-Hydroxy-2-(4-hydroxy-phenyl)-benzo[b]thiophen-3-yl]-[4-(1-methyl-2-piperidin-1-yl-ethoxy)-phenyl]-methanone;

[6-Hydroxy-2-(4-hydroxy-phenyl)-benzo[b]thiophen-3-yl]-[4-(1-methyl-piperidin-2-yl-methoxy)-phenyl]-methanone;

[6-Hydroxy-2-(4-hydroxy-phenyl)-benzo[b]thiophen-3-yl]-[6-(2-piperidin-1-yl-ethoxy)-pyridin-3-yl]-methanone;

[7-Fluoro-6-hydroxy-2-(4-hydroxy-phenyl)-benzo[b]thiophen-3-yl]-[4-(2-piperidin-1-yl-ethoxy)-phenyl]-methanone;

[2-(4-Fluoro-phenyl)-6-hydroxy-benzo[b]thiophen-3-yl]-[4-(2-piperidin-1-yl-ethoxy)-phenyl]-methanone;

{4-[2-(3,4-Dihydro-1H-isoquinolin-2-yl)-ethoxy]-phenyl}-[6-hydroxy-2-(4-hydroxy-phenyl)-benzo[b]thiophen-3-yl]-methanone;

(2-Benzothiazol-6-yl-6-hydroxy-benzo[b]thiophen-3-yl)-[4-(2-piperidin-1-yl-ethoxy)-phenyl]-methanone;

[2-(4-Chloro-phenyl)-6-hydroxy-benzo[b]thiophen-3-yl]-[4-(2-piperidin-1-yl-ethoxy)-phenyl]-methanone;

[6-Hydroxy-2-(tetrahydro-pyran-4-yl)-benzo[b]thiophen-3-yl]-[4-(2-piperidin-1-yl-ethoxy)-phenyl]-methanone;

[6-Hydroxy-2-(4-hydroxy-phenyl)-benzo[b]thiophen-3-yl]-[6-(2-piperidin-1-yl-ethylamino)-pyridin-3-yl]-methanone;

(6-Hydroxy-2-phenyl-benzo[b]thiophen-3-yl)-[4-(2-piperidin-1-yl-ethoxy)-phenyl]-methanone;

[6-Hydroxy-2-(4-hydroxy-phenyl)-benzo[b]thiophen-3-yl]-[4-(3-piperidin-1-yl-prop-1-ynyl)-phenyl]-methanone;

2-(4-Hydroxy-phenyl)-3-[4-(2-piperidin-1-yl-ethoxy)-benzyl]-benzo[b]thiophenol-6-ol;

[4-(2-Cyclobutylamino-ethoxy)-phenyl]-[6-hydroxy-2-(4-hydroxy-phenyl)-benzo[b]thiophen-3-yl]-methanone;

[4-(1-Ethyl-piperidin-2-ylmethoxy)-phenyl]-[6-hydroxy-2-(4-hydroxy-phenyl)-benzo[b]thiophen-3-yl]-methanone;

Especially preferred compounds of the invention include:

{4-[2-(2-Aza-bicyclo[2.2.1]hept-2-yl)-ethoxy]-phenyl}-[6-hydroxy-2-(4-hydroxy-phenyl)-benzo[b]thiophen-3-yl]-methanone;

[6-Hydroxy-2-(4-hydroxy-phenyl)-benzo[b]thiophen-3-yl]-[6-(2-piperidin-1-yl-ethoxy)-pyridin-3-yl]-methanone;

[6-Hydroxy-2-(4-hydroxy-phenyl)-benzo[b]thiophen-3-yl]-[4-(1-methyl-piperidin-2-yl-methoxy)-phenyl]-methanone;

[2-(4-Fluoro-phenyl)-6-hydroxy-benzo[b]thiophen-3-yl]-[4-(2-piperidin-1-yl-ethoxy)-phenyl]-methanone;

[6-Hydroxy-2-(4-hydroxy-phenyl)-benzo[b]thiophen-3-yl]-[4-(3-piperidin-1-yl-prop-1-ynyl)-phenyl]-methanone;

2-(4-Hydroxy-phenyl)-3-[4-(2-piperidin-1-yl-ethoxy)-benzyl]-benzo[b]thiophen-6-ol;

[4-(2-Cyclobutylamino-ethoxy)-phenyl]-[6-hydroxy-2-(4-hydroxy-phenyl)-benzo[b]thiophen-3-yl]-methanone;

[4-(1-Ethyl-piperidin-2-ylmethoxy)-phenyl]-[6-hydroxy-2-(4-hydroxy-phenyl)-benzo[b]thiophen-3-yl]-methanone,

[6-Hydroxy-2-(4-hydroxy-phenyl)-benzo[b]thiophen-3-yl]-{4-[2-(6-methyl-2-aza-bicyclo[2.2.1]hept-2-yl)-ethoxy]-phenyl}-methanone;

Intermediate compounds include the following:

[4-(3-Hydroxy-prop-1-ynyl)-phenyl]-[6-methoxy-2-(4-methoxy-phenyl)-benzo[b]thiophen-3-yl]-methanone;

Methanesulfonic acid 3-{4-[6-methoxy-2-(4-methoxy-phenyl)-benzo[b]thiophene-3-carbonyl]-phenyl}-prop-2-ynyl ester;

(4-Iodo-phenyl)-[6-methoxy-2-(4-methoxy-phenyl)-benzo[b]thiophen-3-yl]-methanone;

[6-Hydroxy-2-(4-hydroxy-phenyl)-benzo[b]thiophen-3-yl]-(4-(piperidine-2-ylmethoxy)-phenyl)-methanone;

[6-Methoxy-2-(4-methoxy-phenyl)-benzo[b]thiophen-3-yl]-(4-hydroxy-phenyl)-methanone;

3-Bromo-6-methoxy-2-(4-methoxy-phenyl)-benzo[b]thiophene.

Trifluoro-methanesulfonic acid 2-(4-methanesulfonyloxy-phenyl)-3-[4-(2-piperidin-1-yl-ethoxy)-benzoyl]-benzo[b]thiophen-6-yl ester.

Pharmaceutical chemists will easily recognize that physiologically active compounds which have accessible hydroxy groups are frequently administered in the form of pharmaceutically acceptable esters or ethers. The literature concerning such compounds, such as estradiol, provides a great number of instances of such esters and ethers. The compounds of this invention are no exception in this respect, and can be effectively administered as an ether or ester, formed on the hydroxy groups, just as one skilled in pharmaceutical chemistry would expect. While the mechanism has not yet been investigated, it is believed that ethers and esters are metabolically cleaved in the body, and that the actual drug, which such form is administered, is the hydroxy compound itself. It is possible, as has long been known in pharmaceutical chemistry, to adjust the rate or duration of action of the compound by appropriate choices of ester or ether groups. For example, the cycloalkyl ethers are known to increase the duration of action of many hydroxy-group-bearing physiologically active compounds.

Certain ether and ester groups are preferred as constituents of the compounds of this invention. The compounds of formula I may contain ester or ether groups at various portions as defined herein above, where these groups are represented as —COOR$^9$, and —OR$^{10}$;

R$^9$ is $C_1$–$C_{14}$ alkyl, $C_1$–$C_3$ chloroalkyl, $C_1$–$C_3$ fluoroalkyl, $C_5$–$C_7$ cycloalkyl, $C_1$–$C_4$ alkoxy, phenyl, or phenyl mono- or disubstituted with $C_1$–$C_4$ alkyl, $C_1$–$C_4$ alkoxy, hydroxy, nitro, chloro, fluoro or tri(clhoro or fluoro) methyl;

R$^{10}$ is $C_1$–$C_4$ alkyl, $C_5$–$C_7$ cycloalkyl or benzyl; and the pharmaceutically acceptable acid addition salts thereof.

The pharmaceutically acceptable acid addition salts of the compounds of this invention may be formed of the compound itself, or of any of its esters or ethers, and include the pharmaceutically acceptable salts which are often used in pharmaceutical chemistry. For example, salts may be formed with inorganic or organic acids such as hydrochloric acid, hydrobromic acid, hydriodic acid, sulfonic acids including such agents as naphthalenesulfonic, methanesulfonic and toluenesulfonic acids, sulfuric acid, nitric acid, phosphoric acid, tartaric acid, pyrosulfuric acid, metaphosphoric acid, succinic acid, formic acid, phthalic acid, lactic acid and the like, most preferable with hydrochloric acid, citric acid, benzoic acid, maleic acid, acetic acid and propionic acid. It is usually preferred to administer a compound of this invention in the form of an acid addition salt, as it is customary in the administration of pharmaceuticals bearing a basic group such as the piperidino ring.

When it is desired to prepare a compound of formula 1 of this invention with one or more ether groups, the ether is prepared by placing the R$^{10}$ moiety on one or more of the hydroxy groups in a manner commonly used for the preparation of ethers. For example, the R$^{10}$ group may be added by reaction with appropriate diazo compound, such as diazomethane, phenyldiazomethane or trimethylsilyldiazomethane (see Hashimoto et al., Tet. Let., 4619–22 (1980).) Such reactions are effectively carried out in solvents including esters such as ethyl acetate, halogenated solvents including dichloromethane and chloroform, and ethers including diethyl ether and tetrahydrofuran. Methanol or boron trifluoride is used as a catalyst, and the process is usually carried out at low temperatures from about −45° C. to about 0° C.

Alternatively, alkylations may be carried out using R$^{10}$X, where X= Br I, mesylate (−OMs), and a base, sodium hydride or potassium carbonate, for example, in a dipolar aprotic solvent such as dimethylformamide at ambient or elevated temperatures.

It is preferable to prepare monoethers by using an ultimate starting compound in the mono-ether form, and using the ether group as a protecting group through the synthesis, protecting other hydroxy groups with an acyl or sulfonyl group.

When a compound is desired with one or more ester groups, it may often be most convenient to prepare the compound using a protecting group other than the desired ester group, hydrolyze off the protecting group and re-acylate one or both of the hydroxy groups at the end of the synthesis. Such acylations are carried out as described below in the discussion of

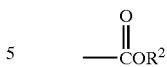

groups as protecting groups. A particularly preferred condition for final acylalions is to use tetrahydrofuran as the solvent and potassium carbonate as the acid scavenger for acylating agents such as acetic anhydride, benzoyl chloride, ethyl chloroformate and the like.

The compounds of this invention, as discussed above, are very often administered in the form of acid addition salts. The salts are conveniently formed, as is usual in organic chemistry, by reacting the compound of this invention with a suitable acid, such as have been described above. The salts are quickly formed in high yields at moderate temperatures, and often are prepared by merely isolating the compound from a suitable acidic wash as the final step of the synthesis. The salt-forming acid is dissolved in an appropriate organic solvent, or aqueous organic solvent, such as an alkanol, ketone or ester. On the other hand, if the compound of this invention is desired in the free base form, it is isolated from a basic final wash step, according to the usual practice. A preferred technique for preparing hydrochlorides is to dissolve the free base in a suitable solvent and dry the solution thoroughly, as over molecular sieves, before bubbling hydrogen chloride gas through it.

The dose of a compound of this invention to be administered to a human is rather widely variable and subject to the judgement of the attending physician. It should be noted that it may be necessary to adjust the dose of a compound when it is administered in the form of a salt, such as a laurate, the salt forming moiety of which has an appreciable molecular weight. The general range of effective administration rates of the compounds is from about 0.05 mg/kg/day to about 50 mg/kg/day. A preferred rate range is from about 1 mg/kg/day to 10 mg/kg/day. Of course, it is often practical to administer the daily dose of compound in portions, at various hours of the day. However, in any given case, the amount of compound administered will depend on such factors as the solubility of the active component, the formulation used and the route of administration.

The route of administration of the compounds of this invention is not critical. The compounds are known to be absorbed from the alimentary tract, and so it is usually preferred to administer a compound orally for reasons of convenience. However, the compounds may equally effectively be administered percutaneously, or as suppositories for absorption by the rectum, if desired in a given instance.

The compounds of this invention are usually administered as pharmaceutical compositions which are important and novel embodiments of the invention because of the presence of the compounds. All of the usual types of compositions may be used, including tablets, chewable tablets, capsules, solutions, parenteral solutions, troches, suppositories and suspensions. Compositions are formulated to contain a daily dose, or a convenient fraction of daily dose, in a dosage unit, which may be a single tablet or capsule or convenient volume of a liquid.

Any of the compounds may be readily formulated as tablets, capsules and the like; it is preferable to prepare solutions from water-soluble salts, such as the hydrochloride salt.

In general, all of the compositions are prepared according to methods usual in pharmaceutical chemistry.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used as well as sodium lauryl sulfate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established in the art.

When it is desired to administer a compound as a suppository, the typical bases may be used. Cocoa butter is a traditional suppository base, which may be modified by addition of waxes to raise its melting point slightly. Water-miscible suppository bases comprising, particularly, polyethylene glycols of various molecular weights are in wide use.

The effect of the compounds may be delayed or prolonged by proper formulation. For example, a slowly soluble pellet of the compound may be prepared and incorporated in a tablet or capsule. The technique may be improved by making pellets of several different dissolution rates and filling capsules with a mixture of the pellets. Tablets or capsules may be coated with a film which resists dissolution for a predictable period of time. Even the parenteral preparations may be made long-acting, by dissolving or suspending the compound in oily or emulsified vehicles which allow it to disperse only slowly in the serum.

The following typical formulae are provided further to assist the formulations chemist.

| CAPSULES | |
|---|---|
| Compound of Formula I | 100 mg |
| Microcrystalline cellulose | 400 mg |
| Pregelatinized starch | 95 mg |
| Silicone fluid | 2 mg |
| Compound of Formula I | 150 mg |
| Pregelatin starch | 106 mg |
| Starch | 52 mg |
| Silicone fluid | 1.6 mg |
| Compound of Formula I | 150 mg |
| Pregelatinized starch | 200 mg |
| TABLETS | |
| Compound of Formula I | 100 mg |
| Microcrystalline cellulose | 240 mg |
| Starch | 45 mg |
| Stearic acid | 6 mg |
| Magnesium stearate | 3 mg |
| Compound of Formula I | 150 mg |
| Microcrystalline cellulose | 128 mg |
| Lactose | 25 mg |
| Pregelantinized starch | 10 mg |
| Stearic acid | 8 mg |
| Magnesium stearate | 3 mg |
| Colloidal silicon dioxide | 2 mg |
| Compound of Formula I | 250 mg |
| Calcium phosphate | 58 mg |
| Lactose | 54 mg |
| Microcrystalline cellulose | 31 mg |

General Methods for the Preparation of Compounds of Formula 1

The methods described in Part 1 illustrate the synthesis of the estrogen agonists of Formula I.

Part 1

Scheme 1 illustrates a general route to compounds I. Methyl 4-hydroxybenzoate is alkylated with 1-bromo-2-chloroethane using sodium ethoxide in refluxing ethanol to yield 1-1. Base hydrolysis and treatment with thionyl chloride produced the acid chloride 1-3 which was used crude. The benzothiophene 1-4, prepared as in Journal of Medicinal Chemistry 27, 1984, 1057, was acylated with 1-3 using triflic acid in refluxing methylene chloride to afford the chloride 1-5. Treatment with sodium iodide in refluxing acetone yields the iodide 1-6. Alkylation of various amines with 1-6 is usually carried out either with potassium or cesium carbonate in DMF. Aromatic heterocycles are N-alkylated by 1-6 by first converting them to sodium salts with sodium hydride in DMF. Basic hydrolysis of 1-7 with potassium hydroxide or potassium carbonate afforded compounds of Formula I. Table 1 lists some of the compounds made by this method. Other protecting groups for the phenols like the methyl ether, which can be deprotected with ethanethiol and aluminum trichloride or by boron tribromide, may also be used. The amines were either commercially available or prepared by known routes. Compound 1-8 is prepared by oxidizing the iodide 1-6 with m-CPBA in methylene chloride followed by basic hydrolysis.

Part 2

The methods described in Part 2 illustrate the preparation of compounds of Formula II. One general approach to some of these compounds is to attach the groups represented by Z to C-3 of a suitably protected benzothiophene 2-1 by Lewis acid catalyzed acylation (Scheme 2). The ketones thus produced can be reduced to the alcohols or methylene analogs 2-3, 2-4 respectively by lithium aluminum hydride or lithium aluminum hydride-aluminum trichloride for example. Deprotection of 2-2, 2-3, 2-4 affords compounds of general formula II.

Alternately, as illustrated in Scheme 3, a suitably protected benzothiophene 2-1 derivative can be brominated, either with bromine buffered with sodium acetate or N-bromosuccinimide in a chlorinated solvent, to yield 3-1 which can be lithiated by tert-butyllithium in THF at −78° C. and quenched with an aldehyde to generate 3-2 which can be oxidized with activated manganese dioxide, for example, and deprotected to afford compounds of Formula II. Compound 3-2 can also be reduced to the methylene compound with sodium borohydride and trifluoroacetic acid, for example.

Scheme 4 illustrates a route to compounds 4-3. Acylation of 2-1 with various chloro or bromo substituted nitrogen containing heterocyclic acid chlorides under aluminum trichloride or other Lewis acids catalysis in methylene chloride or 1,2-dichloroethane yields 4-1. By heating 4-1 with various amines, potassium iodide and sodium bicarbonate or sodium alkoxides in polar solvent, like DMF, 4-2 is prepared. Or 4-1 can be reacted with various alcohols under phase transfer conditions, for example, toluene, sodium hydroxide and 18-crown-6, to afford 4-2. Deprotection of 4-2 to yield 4-3 can be achieved by methods known to those skilled in the art.

Acylation of 2-1 with 4-acetoxybenzoyl chloride is achieved with aluminum trichloride in methylene chloride to yield 5a-1 after base hydrolysis of the acetate. (Scheme 5a) A preferred method to synthesize compound 5a-1 is to acylate 2-1 with p-anisoyl chloride then, to selectively demethylate the methoxy group para to the carbonyl group with lithium ethanethiolate in a polar aprotic solvent like dimethyl formamide at 50 through 80° C. Phenol 5a-1 can be alkylated either with bases like potassium carbonate in acetone or dimethyl formamide and various alkyl halides or mesylates or with various alcohols under Mitsonobu conditions (triphenylphosphine and diethydiazodicarboxylate in tetrahydrofuran to yield compounds 5a-2 and, after deprotection 5a-3. Scheme 5b illustrates a general route to compounds of Formula III. The required starting alcohols 5b-1 are commercially available as the free amines or they can be prepared by reduction of the corresponding acid or esters, for example. They may also be available from the amide 5c-1 by organometallic addition followed by reduction and deprotection to 5b-1 (See Scheme 5C). Mitsonobu coupling to 5a-1 affords 5b-2 which can be debenzylated with hydrogen over Pd/C in alcoholic solvent containing acetic acid to 5b-3. Reductive amination with various aldehydes or ketones leads to 5b-4 then to compounds of Formula III after deprotection.

Iodide 6a-1, prepared by aluminum trichloride acylation of 2-1 with 4-iodobenzoyl chloride, is a valuable intermediate. (Scheme 6a) Heck reaction of 6a-1 and various olefins affords the trans olefins 6a-2 which can be deprotected to provide 6a-3. A typical set of conditions for the Heck reaction is palladium acetate, tri-ortho-tolylphosphine, tributylamine in N-methypyrrolidinone at temperatures varying from room temperature to 120° C. Hydrogenation of 6a-2 over palladium on carbon affords the saturated analogs 6a-4 which can be deprotected to yield 6a-5. Propargyl alcohol and other acetylenic alcohols can be coupled to 6a-1 with cuprous iodide and bistriphenylphosphine palladiumdichloride in triethylamine at room temperature to give 6a-6, mesylation with methanesulfonyl chloride and a tertiary amine base provides 6a-7. Alkylation of various amines afford 6a8. Hydrogenation affords the cis olefins 6a-9, trans-olefins 6a-10 and the saturated compound 6a-5, after deprotection. Vinylation of 6a-1, Scheme 6b, can be achieved by treatment with vinyltributyltin and bistriphenylphosphine palladiumdichloride in refluxing dioxane or dimethoxyethane to afford 6b-1. Oxidative cleavage to the aldehyde 6b-2 can be achieved with catalytic osmium tetroxide and sodium periodate in tert-butanol and water at room temperature. Reduction with mild reducing agents like sodium borohydride yields the alcohol 6b-3 that can be alkylated by various alkyl halides with bases like sodium hydride in tetrahydrofuran or dimethylformamide to give 6b-4. The reactions illustrated in Scheme 6a and 6b can also be used to prepare the corresponding heterocyclic analogs by starting with 6c-1. Compound 6c-1 can be made by acylating 2-1 with heterocyclic acid chlorides substituted with bromides, iodides or trifluoromethanesulfonates.

Compound 3-1 can be metallated with tert-butyllithium in an ethereal solvent at low temperatures, usually −78° C., and the resulting 3-lithiobenzothiophene can be quenched with either carbon dioxide or dimethylformamide to yield the acid, 7-1, or the aldehyde, 7-2, respectively after acid workup. The acid 7-1 can be converted to the Weinreb amide, 7-3, by reaction with N,O-dimethylhydroxylamine and a standard carbodiimide coupling reagent in a chlorinated solvent. The amide 7-3 can be coupled with various Grignard reagents or organolithiums, for example 7-4, to afford the ketones 7-5 after deprotection. The aldehyde 7-2 can be similarly coupled with organometallic reagents to yield 7-5 after oxidation and deprotection.

Part 3

3-Aminobenzenethiol is alkylated on the sulfur by α-bromo4-methoxyacetophenone in ethanolic potassium hydroxide to yield 8a-1. (Scheme 8a) The amine is acetylated by acetic anhydride, 4-dimethylaminopyridine and pyridine in methylene chloride to afford 8a-2. Dehydrative closure of 8a-2 with polyphosphoric acid at 80° C. affords the benzothiophene 8a-3 which was acylated on treatment with 8a-4 for example (prepared as in *Journal of Medicinal Chemistry* 1984, 27, 1057) and aluminum trichloride in methylene chloride to afford 8a-5 after demethylation in the same pot with ethanethiol and aluminum trichloride at room temperature. Hydrolysis of 8a-5 with 5N sodium hydroxide in refluxing ethanol affords the useful intermediate amine 8a-6, which can be formylated with formic acetic anhydride in THF to yield 8a-7 or sulfonylated with sulfonyl chlorides to afford the sulfonamides, like the methylsulfonamide 8a-8. Amine 8a6 can be reacted with other acyl chlorides to form various amides 8a-9 or isocyanates to form carbamates 8a-10 usually with a tertiary amine in methylene chloride.

Scheme 8b outlines the synthesis of 8b-4, a valuable intermediate. As in Scheme 9 using 4-methansulfonyloxy iodobenzene, 8b-1, can be prepared from 6-methoxybenzothiophene, 9-2. Demethylation using boron tribromide in methylene chloride affords 8b-3 which can be reacted with trifluoromethanesulfonic anhydride and 4-dimethylaminopyridine in methylene chloride to afford the triflate 8b-4. Palladium catalyzed carbonylation and methanol quench leads to the methyl ester 8b-5 which can be hydrolysed with aqueous base to the acid 8b-6 that can be reacted with various amines and dicyclohexylcarbodiimide to form amides 8b-7. Alternately palladium catalyzed carbonylation in the presence of tributyltin hydride yields the aldehyde 8b-8 which can reduced to the alcohol 8b-9 with mild reducing agents like sodium borohydride.

Electrophilic fluorination can be carried out on 2-1 by treating with N-fluorobenzenesulfonamide to yield the corresponding fluoride 8c-1. (Scheme 8c) Alternatively lithiation at the C7 position of the benzothiophene occurs with butyllithium in THF, the resulting anion can be quenched with N-halosuccinimide to yield the corresponding bromide and iodide 8c-2, 8c-3 which are also useful intermediates for palladium catalyzed cross-coupling reactions in an ethereal solvent with various alkenyl, aryl or heteroaryl zinc or trialkyltin reagents, which can be prepared from the corresponding Grignards by treatment with zinc chloride or trialkyltin chloride, to prepare 8c-4. A common palladium catalyst is tetrakistriphenylphosphine palladium (0). Compounds 8c-1-4 can be acylated with an acid chloride to provide 8c-5.

Part 4

6-methoxybenzothiophene,9a-2, prepared in two steps from 3-methoxybenzenethiol and 2-bromo-1,1-diethoxyethane (Scheme 9a), is lithiated with n-butyllithium in THF at 0° C. then treated with zinc chloride solution in THF to generate the organozinc reagent that is used immediately in the next step. Cross-coupling between this benzothiophene zinc reagent and alkenyl, aryl or heteroaryl bromides, iodides or triflates is achieved under catalysis by tetrakis (triphenylphosphine)palladium in THF at room temperature or reflux to afford 9a-3 where R is unsaturated. When R is saturated, Scheme 9a is modified slightly. Cross-coupling is carried out as above between the benzothipheneorganozinc and enol triflates (prepared from the corresponding ketones with lithium diisopropylamide then N-phenyltrifluoromethanesulfonimide at −78° C. in THF) with anhydrous lithium chloride added to give, for example, 9a-5 which is hydrogenated over palladium on carbon to yield 9a-6 Both 9a-3 and 9a-5 can be acylated with an acid chloride, like 8a-4, under Lewis acid catalysis, aluminum trichloride or titanium tetrachloride for example, in methylene chloride or dichloroethane at room temperature or at reflux to afford 9a-4 and 9a-7 after standard demethylation with ethanethiol and aluminum trichloride.

Alternately, compound 9a-4 and 9a-7 can be prepared as in Scheme 3, by brominating 9a-3 with bromine, then metal halogen exchange followed by quench with an appropriate aldehyde, oxidation and deprotection.

Alternatively, as in Scheme 9b, 6-methoxybenzothiophene is brominated by N-bromosuccinimide in chloroform at reflux to provide 2-bromo-6-methoxybenzothiophene 9b-1 which can be acylated with acid chlorides like 8a-4 under Lewis acid or triflic acid catalysis in methylene chloride to provide 9b-2. Heck couplings with olefins as described above can provide 2-alkenyl compounds 9b-3 or alkyl 9b-4 after hydrogenation. Alternatively cross-coupling reactions between bromide 9b-2 and aryl or heteroaryl zinc or magnesium reagents catalyzed by palladium (0) catalysts like tetrakis (triphenylphosphine)palladium can provide 2-substituted benzothiophene derivatives 9b-5. Demethylation of 9b-3-5 afford compounds 9b-6.

Scheme 10a describes the synthesis of the indoles 10a-4. A suitably protected amino phenol is heated to around 170° C. with a α-bromoketone to generate the 2-substituted indole 10-1. This may be N-alkylated by deprotonation with a base like sodium amide in tetrahydrofuran and alkylated with various alkyl halides to yield 10a-2. Both 10a-1 and 10-1 can be acylated with acid chlorides to afford the 3-keto indoles 10a-3 which can be deprotected to the desired indoles 10a-4.

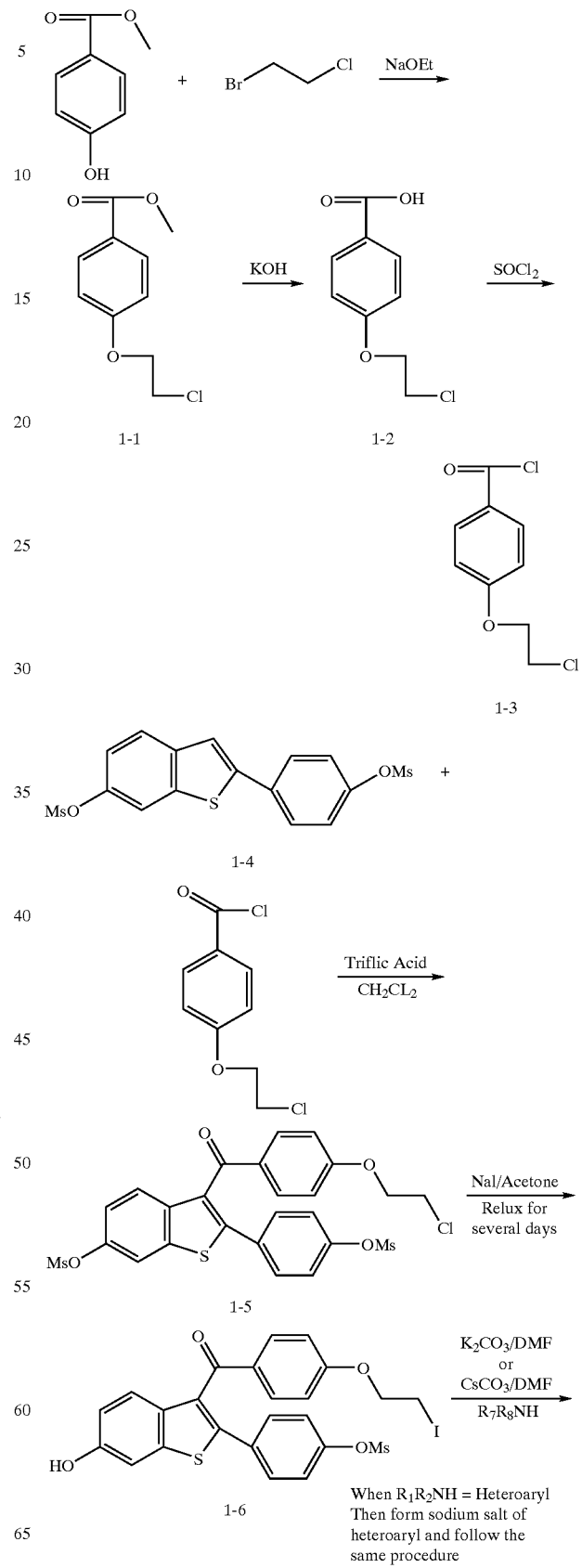

SCHEME 1

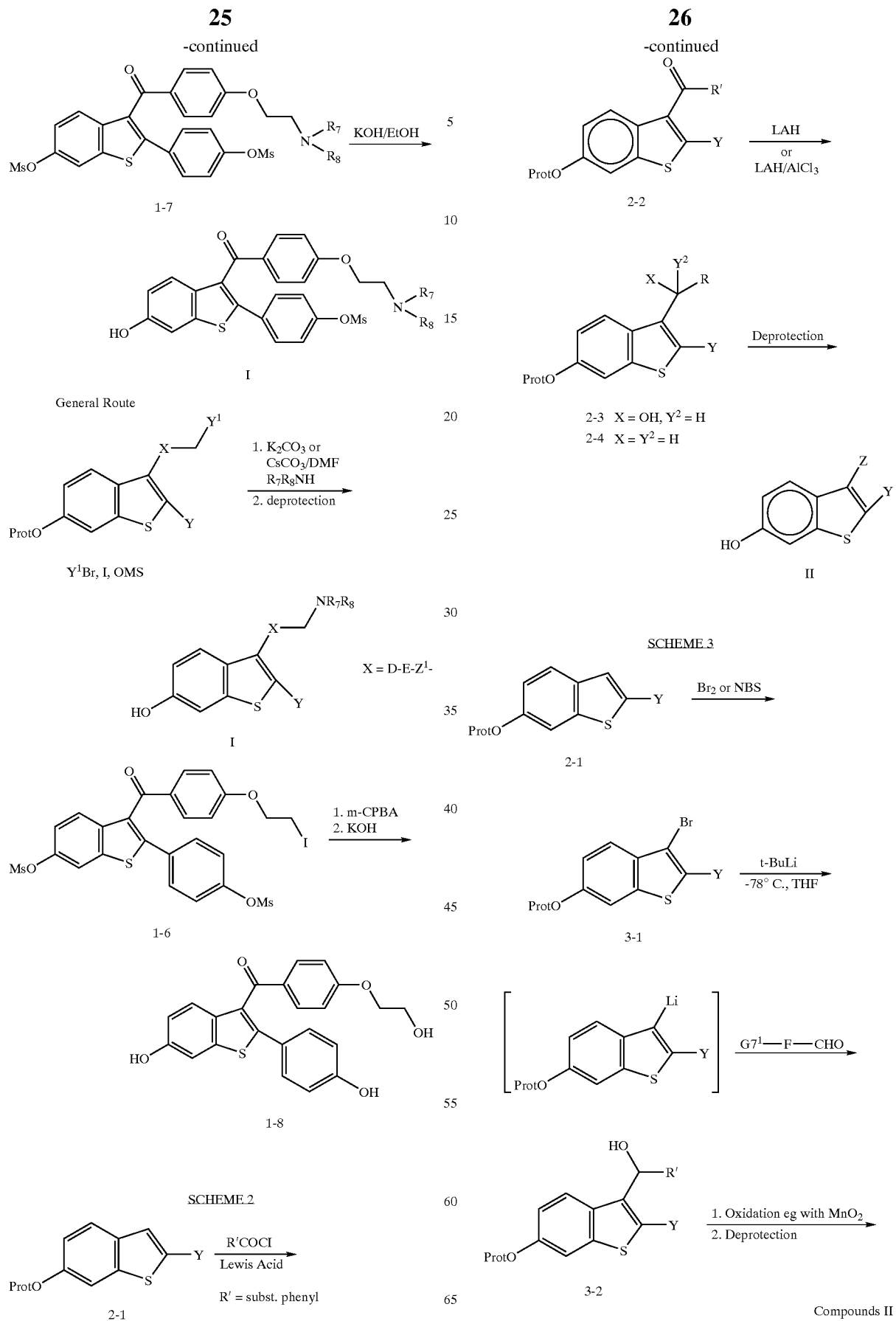

SCHEME 4
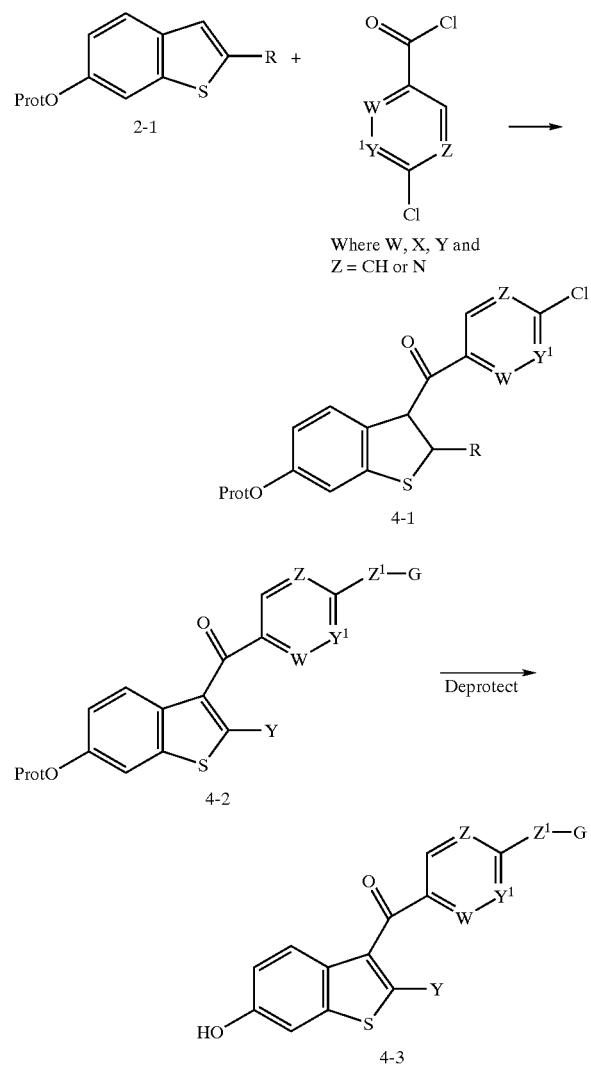
| $Z^1$-G | Example # | W, X, and Y= | Z= |
|---|---|---|---|
| (N-methylpyrrolidine-2-carbonyl piperidine) | 6 | C | N |
| (N-methyl-N-(2-piperidinoethyl)amine) | 5 | C | N |
| (N-methyl-N-(2-piperidinoethyl)amine) | 7 | C | N |
| (2-piperidinoethoxy) | 8 | C | N |
SCHEME 5a
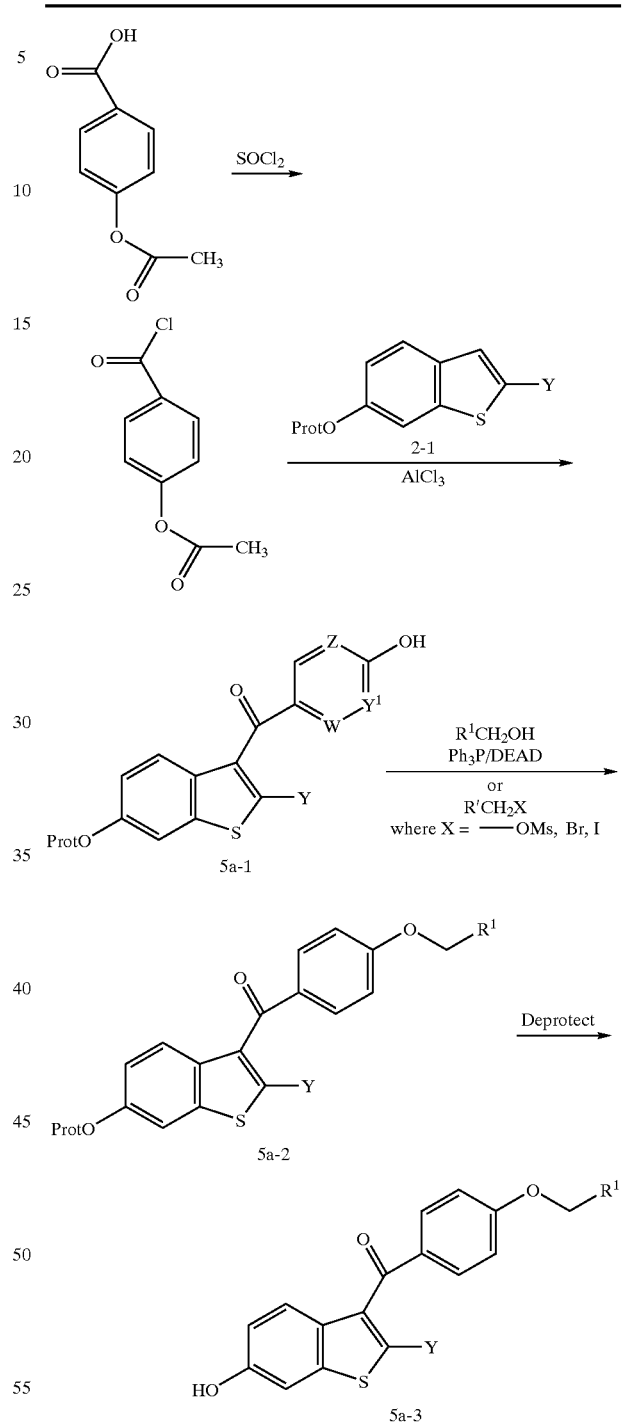
| EXAMPLE # | $R^1$= |
|---|---|
| 10 | 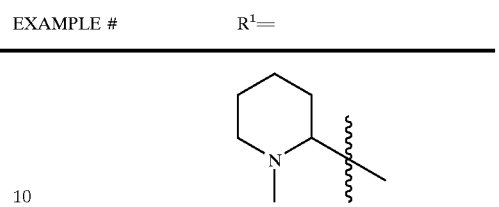 |

SCHEME 5a-continued
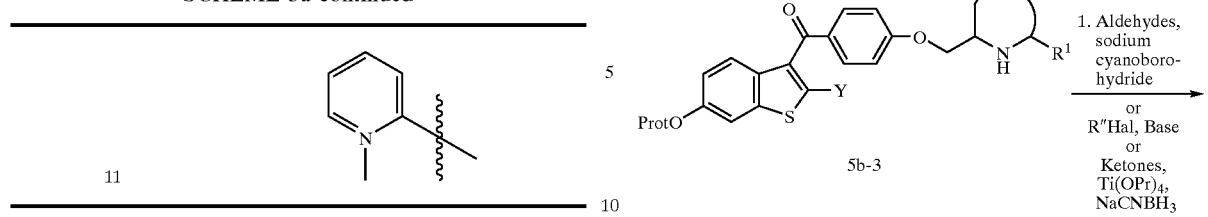
SCHEME 5b
Synthesis of compounds of Formula III
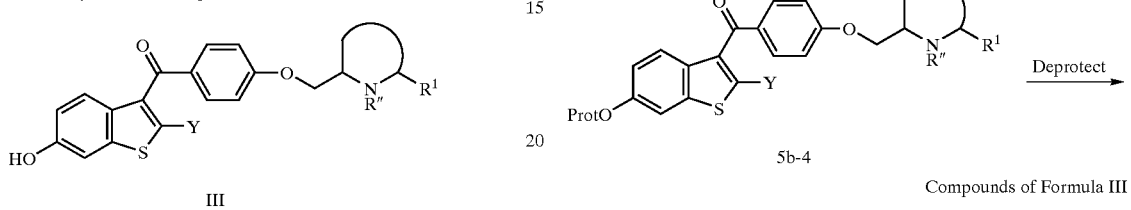
R″ = an amine protecting group, eg. Bz
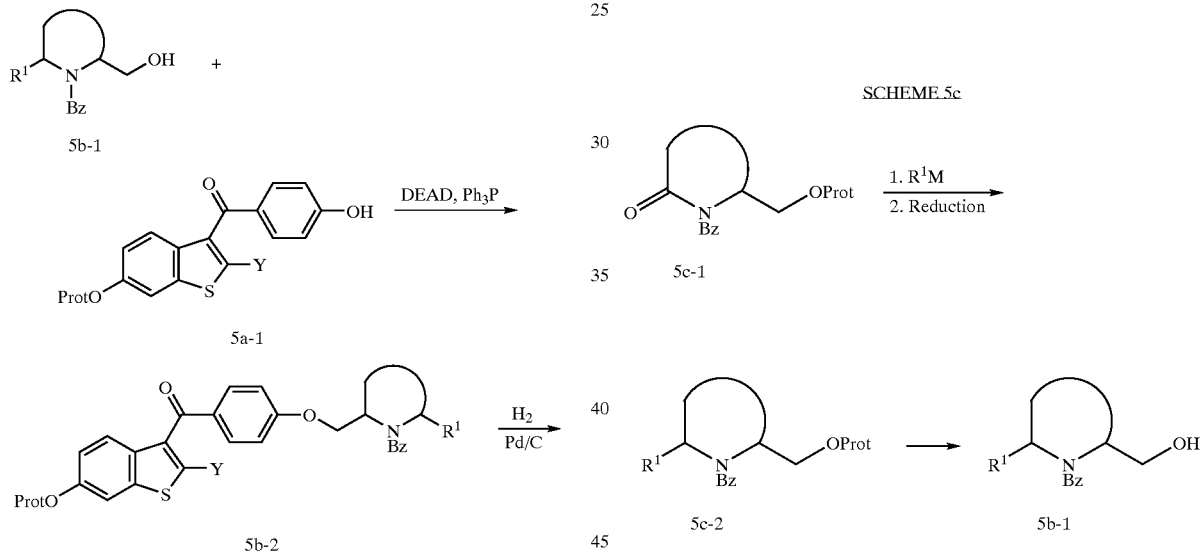
SCHEME 6a
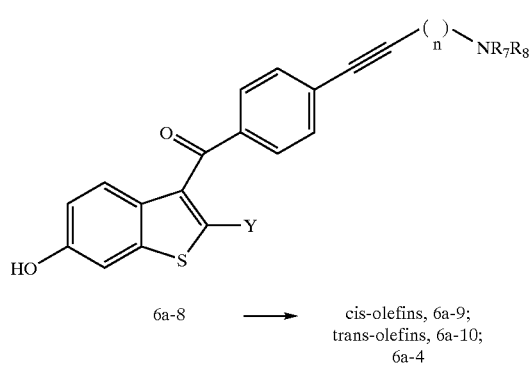
cis-olefins, 6a-9;
trans-olefins, 6a-10;
6a-4

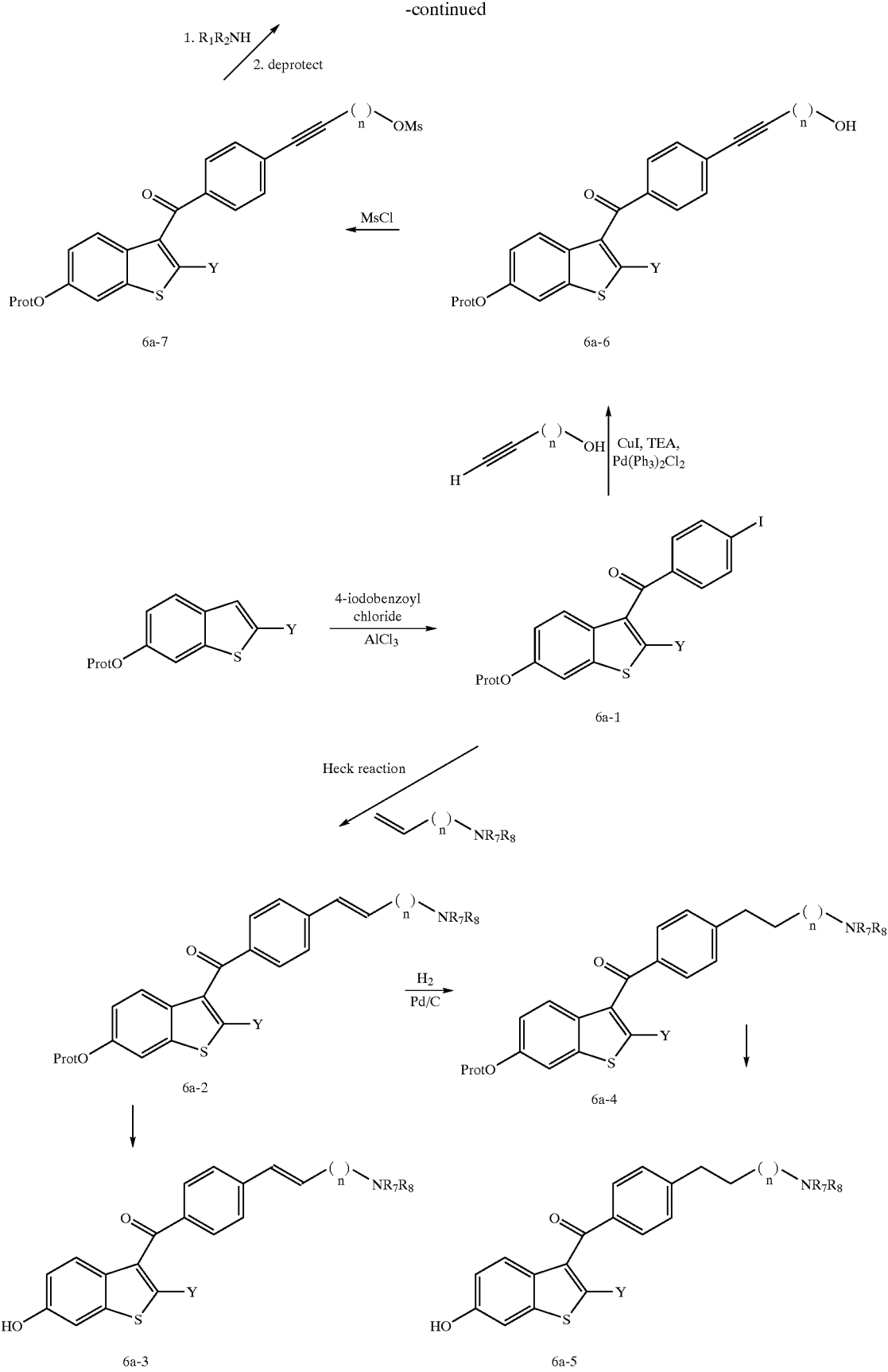

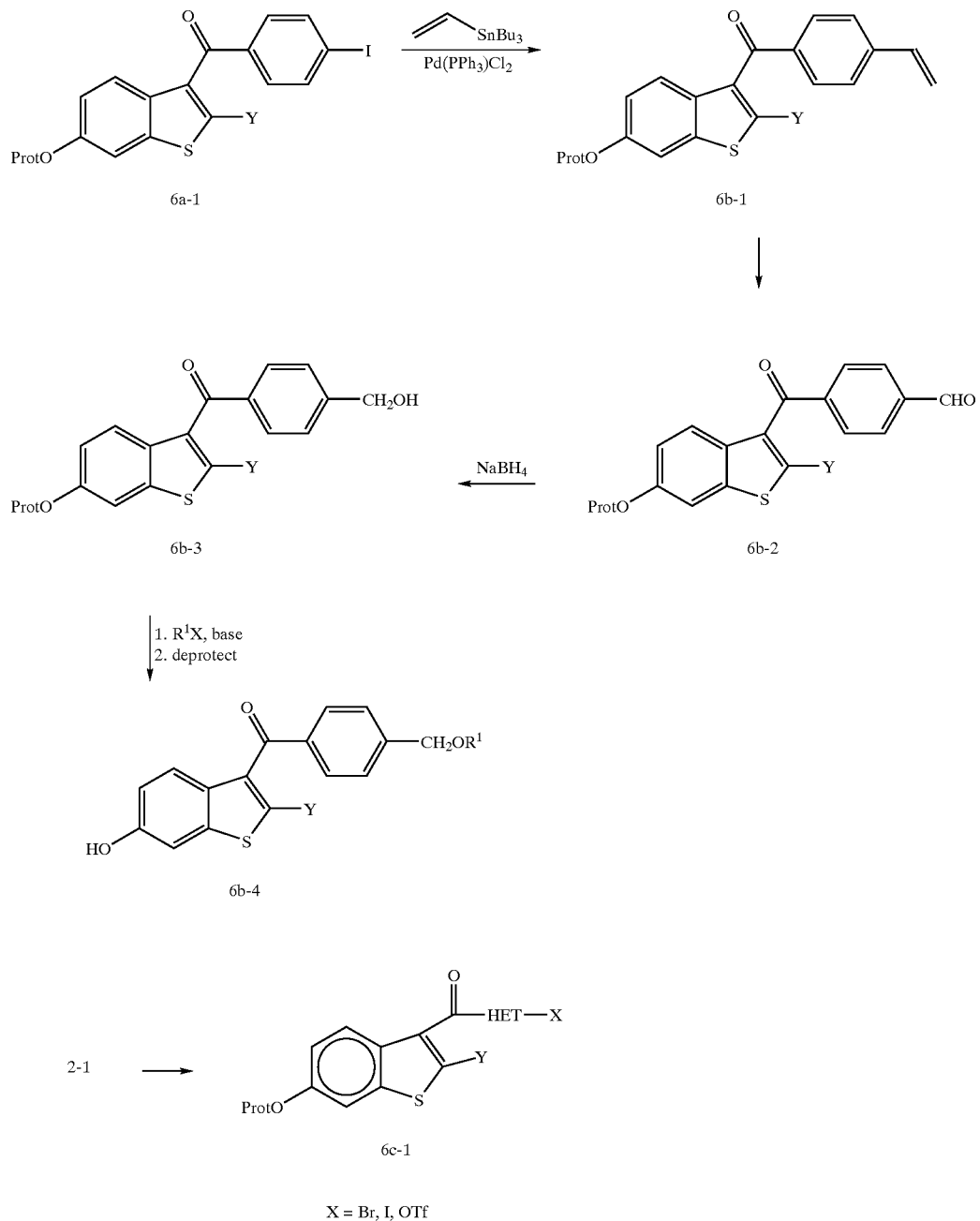
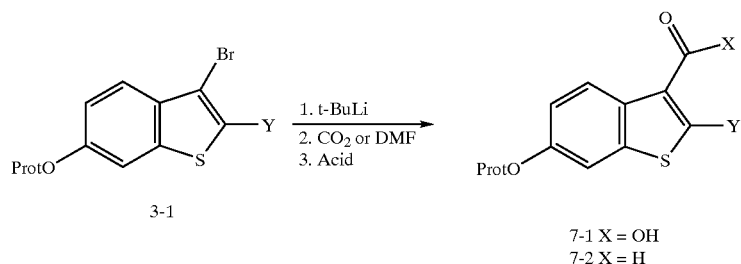

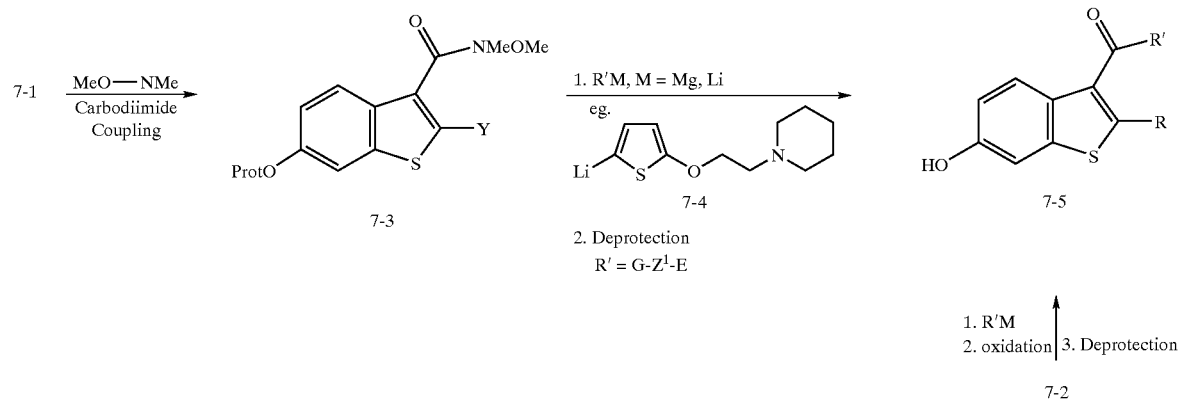
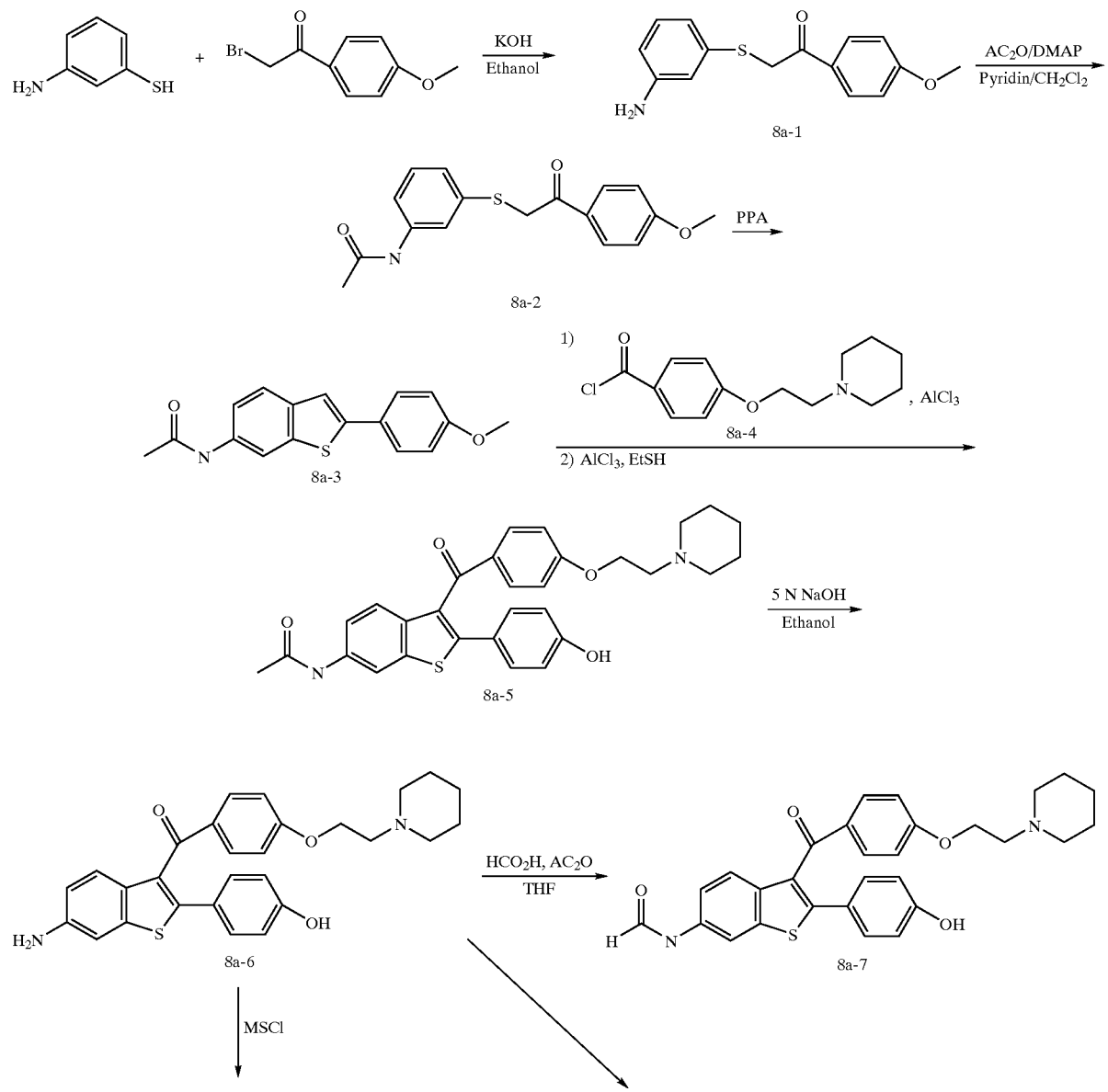
SCHEME 8a

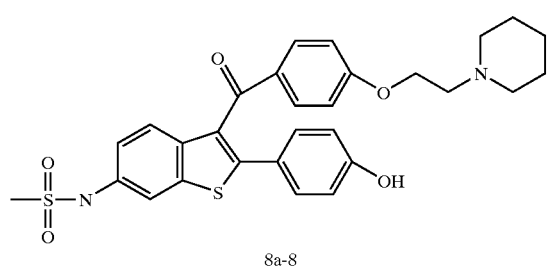
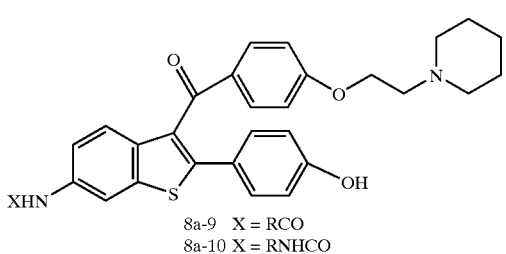
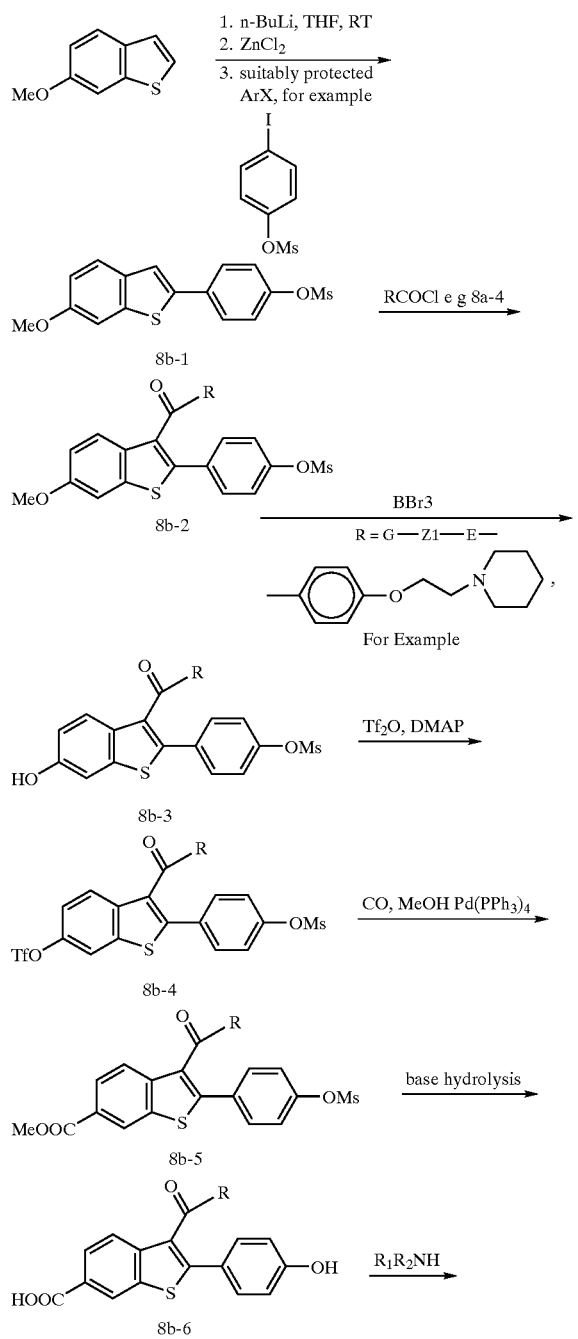
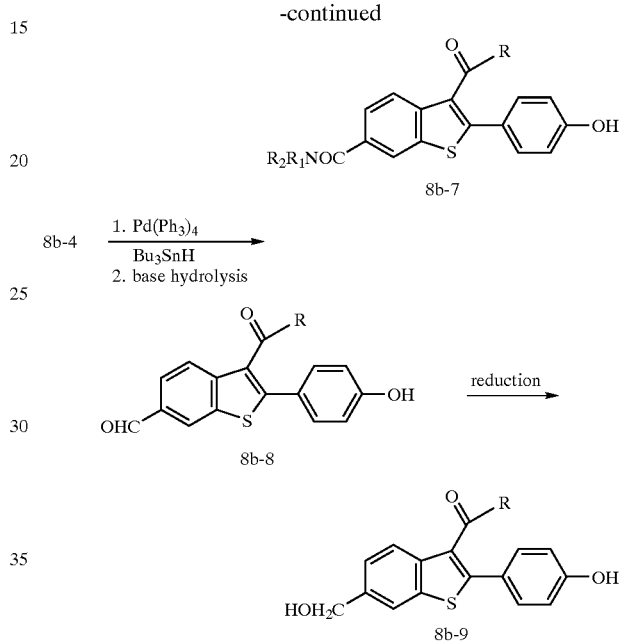
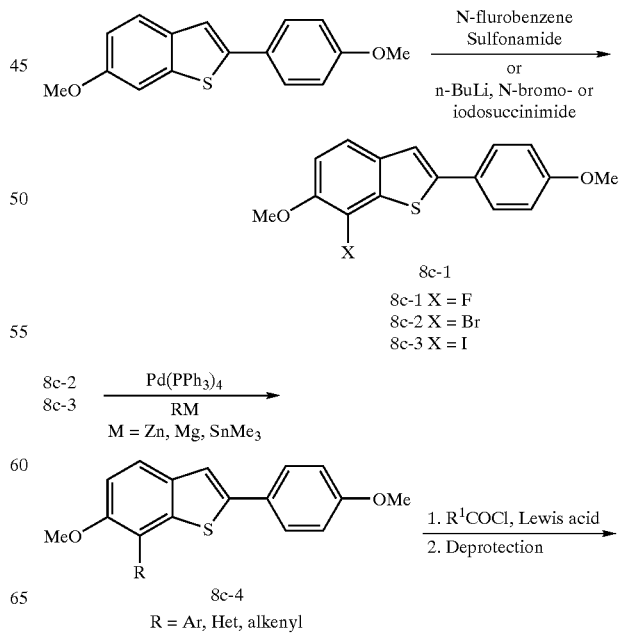

-continued
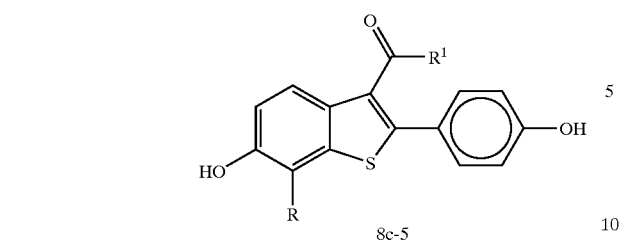
SCHEME 9A
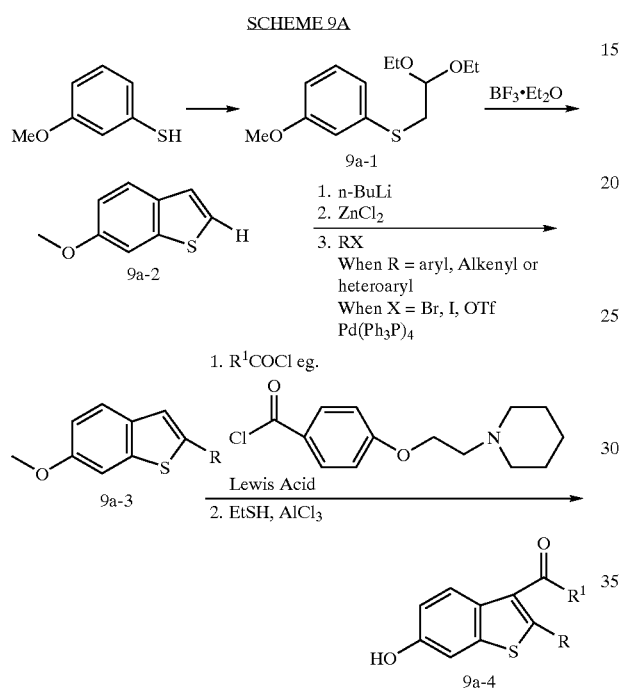
When R is saturated, for example, R = cyclohexyl then:
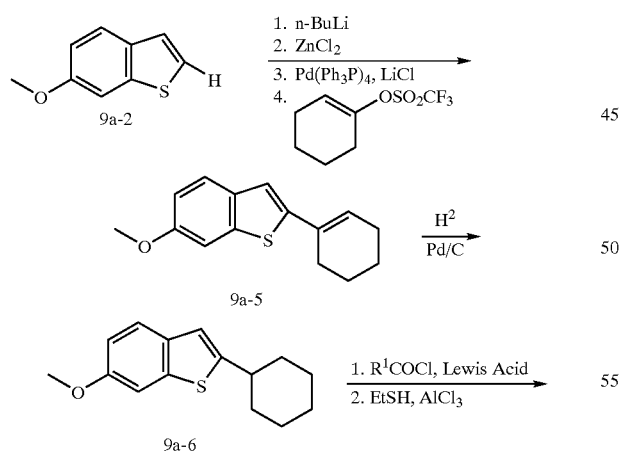
SCHEME 9b
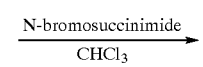
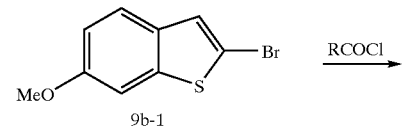
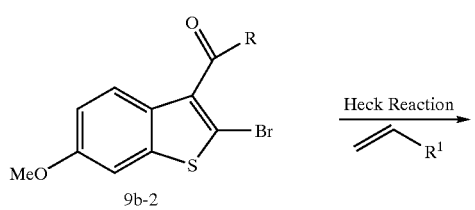
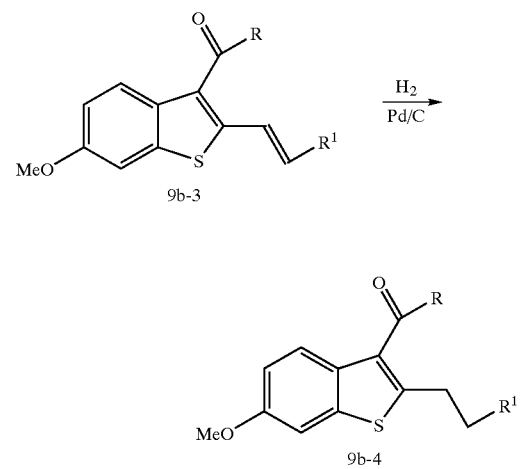

SCHEME 10a

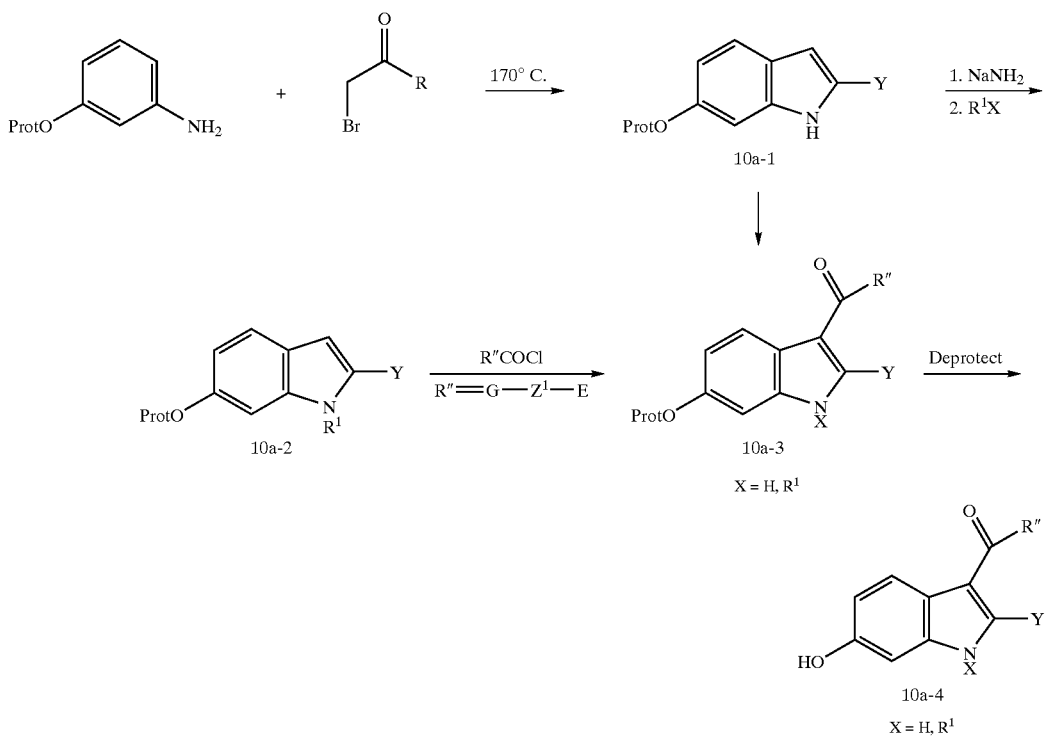

10a-1

10a-2

10a-3
X = H, R¹

10a-4
X = H, R¹

EXAMPLES

1H-NMR spectra were recorded on a Bruker AC250 spectrometer. Reactions were usually performed under a nitrogen atmosphere. Anhydrous solvents were purchased from Aldrich Chemical Company and were used as received. Tetrahydrofuran (THF) was distilled from sodium/benzophenone prior to use. Commercially available reagents were used as received unless otherwise noted. Thin layer chromatography was performed on E. Merck Kieselgel 60 F254 plates (0.25 mm) and flash column chromatography was performed using EM Science Silica Gel 60. Chromatography solvent mixtures are reported as volume ratios. Compounds of general Formula I are made by the reactions outlined in Scheme 1 herein above. Synthesis of the key intermediate methanesulfonic acid 3-[4-(2-iodo -ethoxy)-benzoyl]-2-(4-methanesufonyloxy-phenyl)-benzo[b]thiophen-6-yl ester, then a general procedure to compounds of Formula I is described.

Example 1
Step 1

4-(2-Chloro-ethoxy)-benzoic acid methyl ester. To 35 mL of ethanol was added sodium pellets (2.27gm, 98.6 mmol). After all the sodium had disappeared methyl-4-hydroxybenzoate (15 gm, 98 mmol) was added in one portion at room temperature. The reaction mixture was then heated to 60° C. and treated dropwise with 1-bromo-2-chloroethane (10.2 gm, 123 mmol) in 15 mL of ethanol. The reaction was stirred for 16 hrs then cooled to room temperature and concentrated. The residue was taken up in ethyl acetate and washed with water, 2N NaOH, and brine. The organic layer was dried over anhydrous magnesium sulfate, filtered, and concentrated. The crude product was chromatographed on silica gel using 1:10 Ethyl acetate:Hexanes to 1:6 Ethyl acetate:Hexanes as the gradient eluant to yield 11.9 gm of the title compound.

Step 2

4-(2-Chloro-ethoxy)benzoic acid. To methyl 4-(2-Chloroethoxy)-benzoic acid (11.8 gm, 53.5 mmol) dissolved in 118 mL of methanol was added 2N KOH (35mL, 1.3 equiv.) and the resulting solution was heated at 50° C. for 24 hrs. The reaction was cooled to room temperature and the methanol evaporated off. The residue was diluted with water and extracted once with ethyl acetate. The aqueous layer was then acidified with 6N HCl and a precipitate formed which was filtered off, washed well with water, and pumped dry under vacuum to yield 10 gm of the title compound.

Step 3

Methanesulfonic acid 3-[4-(2-chloro-ethoxy)-benzoyl]-2-(4-methanesulfonyloxy-phenyl)-benzo[b]thiophen-6-yl ester. The product from step 2 (654 mg, 3.26 mmol) was stirred with thionyl chloride (1.2 mL) for 3 hrs at 50° C. Then the excess thionyl chloride was removed by vacuum distillation. Azeotroping with benzene removed any residual thionyl chloride. The residue was dissolved in methylene chloride (29 mL) and methanesulfonic acid 2-(4-methanesulfonyloxy -phenyl)-benzo[b]thiophen-6-yl ester[1] (1 gm, 2.5 mmol) and triflic acid (0.78 mL) were added. The reaction was stirred at reflux overnight. The reaction was not complete therefore another equivalent of acid chloride was added and the reaction stirred a further 3 hours until complete. The mixture was cooled to 0° C. and saturated sodium bicarbonate solution was added slowly. The organic layer was separated and washed once with water, dried over anhydrous sodium sulfate, filtered, and concentrated. The residue was chromatographed on silica gel using 1:1 Ether:

Petroleum Ether to 7:1 Ether:Petroleum Ether as the gradient eluant to yield 886 mg of the title compound.

1. *Journal of Medicinal Chemistry*, 1984, 27, 1057.

Step 4

Methanesulfonic acid 3-[4-(2-iodo-ethoxy)-benzoyl]-2-(4-methanesulfonyloxy-phenyl)-benzo[b]thiophen-6-yl ester. A solution of the product from step 3 (3.5 gm, 1 equiv.) and NaI (9.02 gm, 10 equiv.) in 50 mL of Acetone was heated at reflux for 2 days until the reaction was complete. The reaction was cooled and concentrated to a solid. The residue was dissolved in ethyl acetate, washed with water and brine, dried over anhydrous magnesium sulfate, filtered, and concentrated to yield 3.5 gm of the title compound.

General Procedure to alkylate primary and secondary amines with methanesulfonic acid 3-[4-(2-iodo-ethoxy)-benzoyl]-2-(4-methanesulfonyloxy-phenyl) -benzo[b] thiophen-6-yl ester (the product from step 4) followed by base hydrolysis to yield compounds of Formula I. An example is given using 2-Aza-bicyclo[2.2.1]heptane as the amine.

Step 5

Methanesulfonic acid 3-{4-[2-(2-aza-bicyclo[2.2.1]hept-2-yl)-ethoxy]-benzoyl}-2-(4-methanesulfonyloxy-phenyl)-benzo[b]thiophen-6-yl ester. A solution of the product from step 4 (3-[4-(2-iodo-ethoxy)-benzoyl]-2-(4-methanesulfonyloxy-phenyl)-benzo[b]thiophen-6-yl ester) (0.26 mmol), 2-Aza-bicyclo[2.2.1]heptane (0.28 mmol), and either potassium carbonate or cesium carbonate (0.7 mmol) as the base in 5 mL of DMF was stirred at room temperature for 16 hrs. The reaction was then concentrated and the residue was taken up in ethyl acetate, washed with water, and brine. The organic layer was dried over anhydrous magnesium sulfate, filtered, and concentrated to yield 111 mg of the title compound. This can be used crude in the hydrolysis step or preferably purified by silica gel chromatography.

Step 6

{4-[2-(2-Aza-bicyclo[2.2.1]hept-2-yl)-ethoxy]-phenyl}-[6-hydroxy-2-(4-hydroxy-phenyl)-benzo[b]thiophen-3-yl]-methanone. A solution of the product from Step 5 (111 mg, 0.17 mmol) and potassium carbonate (7.5 equiv.) in 10 mL of methanol was heated at 50° C. for 48 hrs. The mixture was concentrated to a solid. This solid was chromatographed on silica gel using 1% MeOH/methylene chloride to 20% MeOH/methylene chloride as the gradient eluant to yield the desired product which was then made into the its hydrochloride salt with hydrogen chloride in dioxane.

Alternatively, the product from Step 5 can be hydrolysed by refluxing with 250 mL 5N sodium hydroxide in 5 mL of ethanol for one hour. The reaction is acidified with 3 N HCl to about pH5 then saturated sodium bicarbonate is added and the whole extracted with chloroform (about half volume of methanol is added if necessary to dissolve the organics). The organic layer is washed with brine and dried over anhydrous sodium sulfate. After concentration and silica gel chromatography, usually with 2–7% methanol in methylene chloride with 1–5% ammonium hydroxide if needed, the product is obtained as a foam. This is converted to the HCl salt as above.

When the nitrogen being alkylated is contained in a heterocycle the reaction is performed as below with imidazole being used as the example.

Example 2

Step 1

Methanesulfonic acid 3-[4-(2-imidazol-1-yl-ethoxy)-benzoyl]-2-(4-methane -sulfonyloxy-phenyl)-benzo[b] thiophen-6-yl ester. To mixture of sodium hydride (0.33 mmol) in 10 mL of dimethylformamide was added imidazole (0.30 mmol) and stirred at room temperature for 15 min. To this mixture was added (3-[4-(2-iodo-ethoxy)-benzoyl]-2-(4-methanesulfonyloxy-phenyl)-benzo[b]thiophen-6-yl ester) (0.22 mmol), and the reaction was stirred at room temperature for 16 hrs. It was concentrated and the residue was taken up in ethyl acetate and washed with water. The organic layer was then washed with brine, dried over Anhydrous magnesium sulfate, filtered, and concentrated to yield the title compound.

Step 2

[6Hydroxy-2-(4-hydroxy-phenyl)-benzo[b]thiophen-3-yl]-[4-(2-imidazol-1-yl-ethoxy)-phenyl]-methanone. The mesylate protecting groups on the product from Step 1 were removed by base hydrolysis using either potassium carbonate in methanol or sodium hydroxide in ethanol as in Step 6 of Example 1 to yield the title compound.

$^1$H NMR (MeOH-d$_4$) δ7.75(m, 3H), 7.45(d, 1H), 7.29(d, 1H), 7.20(d, 1H), 7.18(d, 2H), 7.00(s, 1H), 6.85(m, 3H), 6.60(d, 2H), 4.40(t, 2H), 4.30(t, 2H)

Table 1 lists some of the examples made by these two procedures along with relevant data.

Example 3

Step 1

Methanesulfonic acid 3-[4-(2-hydroxy-ethoxy)-benzoyl]-2-(4-methanesulfonyloxy-phenyl)-benzo[b]thiophen-6-yl ester. A solution of (3-[4-(2-iodo-ethoxy)-benzoyl]-2-(4-methanesulfonyloxy-phenyl)-benzo[b]thiophen-6-yl ester) (0.03 mmol) and m-chloroperoxybenzoic acid (0.036 mmol) in 5 mL of methylene chloride was stirred at room temperature for 16 hrs. at which time an additional 0.036 mmol of M-Chloroperoxybenzoic acid was added and the reaction heated to 50° C. for 16 hrs. The reaction was extracted into methylene chloride from saturated sodium bicarbonate solution. The organic layer was dried over anhydrous magnesium sulfate, filtered, and concentrated to yield the title compound.

Step 2

[4-(2-Hydroxy-ethoxy)-phenyl]-6-hydroxy-2-(4-hydroxy-phenyl)-benzo[b]-thiophen-3-yl]-methanone. The mesylate protecting groups on the title compound from Step 1 were removed using the methods outlined in Example 1, Step 6 to obtain the title compound.

Mass Spectroscope: M$^+$=406

Tlc: R$_1$=0.50 (9:1 Chloroform/Methanol)

Example 4

Step 1

4-(1-Methyl-2-piperidin-1-yl-ethoxy)-benzoic acid methyl ester. To a solution of methyl-4-hydroxy benzoate (13 mmol) and α-methyl-1-piperidine ethanol (13 mmol) in 40 mL of tetrahydrofuran was added triphenylphosphine (16.9 mmol). At 0° C., DEAD (diethyl azodicarboxylate) (15.6 mmol) was added dropwise. After the addition was complete, the reaction was allowed to warm to room temperature and stirred for 1 hr. The reaction was then concentrated to dryness and the residue was taken up in EtOAc, and the product was extracted into 1 N hydrochloric acid. The aqueous layer was made basic with 5N NaOH and extracted three times with EtOAc. The combined organics were then washed with brine, dried over MgSO$_4$, filtered, and concentrated. Chromatography on silica gel using 30% THF/ hexanes afforded two isomeric products the title compound and 4-(2-piperidin-1-yl-propoxy)-benzoic acid methyl ester.

Step 2

4-(1-Methyl-2-piperidin-1-yl-ethoxy)-benzoic acid. A solution of 4-(1-Methyl-2-piperidin-1-yl-ethoxy)-benzoic acid methyl ester, from Step 1, Example 4, (0.69 g, 2.49 mmol) and 1.5 mL of 2N NaOH in 2 mL of methanol was heated to reflux for 2 hrs. The reaction mixture was then diluted with water and washed with ethyl acetate to remove any by-products. The aqueous layer was concentrated to dryness and chromatographed on a reverse phase silica column using 20% MeOH in 80% Buffer (0.1% TFA in water) as the eluant to yield the title compound as its trifluoroacetate salt.

Step 3

4-(1-Methyl-2-piperidin-1-yl-ethoxy)-benzoyl chloride. To a solution of the product from Step 2, Example 4 (2.07 mmol) in 27 mL of chlorobenzene was added 3 drops of dimethylformamide and thionyl chloride (35.1 mmol) and the solution was heated to 75° C. for 2.5 hrs. The reaction was then cooled to room temperature and the excess thionyl chloride and chlorobenzene was removed in vacuo. Theoretical yield was assumed and the residue was dissolved in 6.16 mL of dichloromethane (i.e., 1 mL of solution=100 mg of the title compound). The solution was used in the next step of the synthesis without further purification.

Step 4

[6-Hydroxy-2-(4-hydroxy-phenyl)-benzo[b]thiophen-3-yl]-4-(1-methyl-2-piperidin-1-yl-ethoxy)-phenyl]-methanone. To a dichloromethane solution of the title compound from Step 3 (3.33 mmol) was added 35 mL of dichloromethane, 6-methoxy-2-(4-methoxyphenyl)-benzo[b]thiophene (1 g, 3.7 mmol), and $AlCl_3$ (3.7 g, 27.8 mmol) and the resulting mixture was stirred for 2 hrs. at room temperature. Demethylation was accomplished by adding ethanethiol (1.06 mL, 14.4 mmol) and stirring for a further hour. The reaction was quenched with saturated sodium bicarbonate solution and extracted with chloroform containing enough methanol (about 3/1 chloroform-methanol)to dissolve the organics. If needed the aluminum salts can be filtered off through a Celite pad prior to separation of the layers. The combined organic layers were washed with brine and dried over anhydrous magnesium sulfate. Filtration, concentration and chromatography on silica gel using 5% methanol in dichloromethane as the eluant afforded the title compound (800 mg) as a yellow foam. The title (360 mg) was converted to the hydrochloride salt by dissolving in 500 mL-1 mL of dioxane and adding a solution of hydrogen chloride in dioxane. The solid that precipitates is filtered off and washed with ether to yield the hydrochloride salt of the title compound as a tan solid.

$^1$H NMR (MeOD) δ7.70(d, 2H), 7.45(d, 1H), 7.25(d, 1H), 7.15(d, 2H), 6.85(m, 3H), 6.60(d, 2H), 3.75(t, 1H), 2.65(m, 1H), 2.50(m, 5H), 1.60(m, 4H), 1.45(m, 2H), 1.20(d, 3H)

Example 5

Step 1

(6-Chloro-pyridin3-yl)-[6-methoxy-2-(4-methoxy-phenyl)-benzo[b]thiophen-3-yl]-methanone. To a suspension of 2-Chloropyridine-5-carbonyl chloride (4.23 gm, 24 mmol) and 6-Methoxy-2-(4-methoxy-phenyl)-benzo[b]thiophene (5.0 gm, 18.5 mmol) in 275 mL of methylene chloride was added aluminum trichloride (18.59 g, 138.8 mmol) in three portions. The black-red reaction was stirred for 16 hrs. at room temperature. The reaction was then quenched with 400 mL of 2N NaOH (slowly and cooled in ice) and extracted into 300 mL of methylene chloride. The organic layer was washed with brine, dried over anhydrous sodium sulfate, filtered, and concentrated to a yellow solid which was chromatographed on silica gel using 5% to 20% Ethyl acetate/Hexanes as the gradient eluant to yield 2.47 gm of the title compound.

Step 2

[6-Methoxy-2-(4-methoxy-phenyl)-benzo[b]thiophen-3-yl]-[6-(2-piperidin-1-ylmethyl-pyrrolidin-1-yl)-pyridin-3-yl]-methanone. A solution of the product from Step 1, Example 5 (250 mg, 0.61 mmol), sodium bicarbonate (66.7 mg, 0.79 mmol), potassium iodide (50.7 mg, 0.31 mmol), and 1-Pyrrolidin-2-ylmethyl-piperidine[2] (308 mg, 1.83 mmol) in 3 mL of Ethanol was heated at reflux for 16 hrs. The solvent was evaporated off and the residue was diluted with water and extracted with methylene chloride. The organics were dried over anhydrous magnesium sulfate, filtered, and concentrated. The residue was chromatographed on silica gel using 3% MeOH : 2% aqueous $NH_4OH$: 95% methylene chloride as the eluant to obtain 261 mg of the title compound.

2. *Journal of Medicinal Chemistry* 1992, 35, 4334

Step 3

[6-Hydroxy-2-(4-hydroxy-phenyl)-benzo[b]thiophen-3-yl]-[6-(2-piperidin-1-yl-ethylamino)-pyridin-3-yl]-methanone. To a solution of the product from Step 2, Example 5 (230 mg, 0.42 mmol) in 3 mL of methylene chloride at 0° C. was added dropwise boron tribromide (2 mL, 1 mM in $CH_2Cl_2$, 2 mmol). The reaction was allowed to warm to room temperature and stirred for 2 hrs. The reaction was quenched with saturated sodium bicarbonate solution and extracted three times with chloroform. The combined organic layer was dried over sodium sulfate and concentrated to a yellow solid which was then chromatographed on silica gel using 1% MeOH:1% $NH_4OH$: 98% methylene chloride to 3% MeOH:1% $NH_4OH$: 96% methylene chloride as the gradient eluant to yield 67 mg of the title compound.

$^1$H NMR (MeOH-d4) δ8.25(s, 1H), 7.85(s, 1H), 7.50(d, 1H), 7.25(m, 3H), 6.95(dd, 1H), 6.70(d, 2H), 6.45(d, 1H), 3.50(t, 2H), 2.55(m, 6H), 1.55(m, 6H)

Example 6

Step 1

[6-Methoxy-2-(4-methoxy-phenyl)-benzo[b]thiophen-3-yl]-{6-[2-(piperidine-1-carbonyl)-pyrrolidin-1-yl]-pyridin-3-yl}-methanone. The coupling of the product from Step1, Example 5 (6-Chloro-pyridin-3-yl)-[6-methoxy-2-(4-methoxy -phenyl)-benzo[b]thiophen-3-yl]-methanone) and piperidin-1-yl-pyrrolidin-2-yl -methanone[2] was accomplished by the procedure set forth in Example 5, Step 2 to afford the title compound.

Step 2

[6-Hydroxy-2-(4-hydroxy-phenyl)-benzol[b]thiophen-3-yl]-{6-[2-(piperidine-1-carbonyl)-pyrrolidin-1-yl]-pyridin-3-yl}-methanone. Demethylation of the product from Step 1, Example 6 was carried out as in Example 5, Step 3 to yield the title compound.

$^1$H NMR (MeOH-$d_4$) δ8.25(d, 1H), 7.85(d, 1H), 7.30(d, 1H), 7.20(m, 3H), 6.85(d, 1H), 6.60(d, 2H), 6.40(bs, 1H)

Example 7

Step 1

[6-Methoxy-2-(4-methoxy-phenyl)-benzo[b]thiophen-3-yl]-[6-(2-piperidin-1-yl-ethylamino)-pyridin-3-yl]-methanone. The coupling of the product from Step 1, Example 5 (6-Chloro-pyridin-3-yl)-[6-methoxy-2-(4-methoxy-phenyl) -benzo[b]thiophen-3-yl]-methanone) and 1-(2-Aminoethyl)-piperidine was carried out as in Example 5, Step 2 to give the title compound.

Step 2

[6-Hydroxy-2-(4-hydroxy-phenyl)-benzo[b]thiophen-3-yl]-[6-(2-piperidin-1-ylmethyl-pyrrolidin-1-yl)-pyridin-3-yl]-methanone. Demethylation of the product from Step 1, Example 7 was carried out using the procedure in Example 5, Step 3 to obtain the title compound.

$^1$H NMR (MeOH-$d_4$) δ8.25(s, 1H), 7.85(d, 1H), 7.45(d, 1H), 7.20(m, 3H), 6.85(dd, 1H), 6.65(d, 2H), 6.45(d, 1H), 3.50(m, 1H), 3.35(d, 2H), 2.45(m, 6H), 2.00(m, 4H), 1.50 (m, 6H)

Example 8
Step 1

[6-(2-piperidinyl-1-yl-ethoxy)-pyridin-3-yl]-[6-methoxy-2-(4-methoxy -phenyl)-benzo[b]thiophen-3-yl]-methanone. The coupling of the product from Step 1, Example 5 (6-Chloro-pyridin-3-yl)-[6-methoxy-2-(4-methoxy-phenyl)-benzo[b]thiophen-3-yl]-methanone) and 1-piperidineethanol sodium salt was carried out as in Example 5, Step 2 to yield the title compound.

A preferred method is to use phase transfer conditions. The product from Step 1, Example 5 (6-Chloro-pyridin-3-yl)-[6-methoxy-2-(4-methoxy-phenyl) -benzo[b]thiophen-3-yl]-methanone) (890 mg, 2.17 mmol), 1-piperidineethanol (365 mg, 2.8 mmol), potassium hydroxide (256 mg, 4.56 mmol, crushed in a mortar), 18-crown-6 (57 mg, 0.2 mmol) in 20 mL of toluene was stirred overnight at room temperature. The reaction was diluted with ethyl acetate and washed with water. The organic layer was washed with brine, dried over anhydrous magnesium sulfate, filtered and concentrated. The residue was chromatographed on silica gel using 1:1 ethyl acetate to pure ethyl acetate as the gradient eluant to yield 920 mg of the title compound.

Step 2

[6-Hydroxy-2-(4-hydroxy-phenyl)-benzo[b]thiophen-3-yl]-[6-(2-piperidin-1-yl-ethoxy)-pyridin-3-yl]-methanone. The methyl protecting groups on the product from Step 1, Example 8 were removed by the procedure in Example 5, Step 3 to obtain the title compound.

$^1$H NMR (MeOH-d$_4$) δ8.35(s, 1H), 8.05(d, 1H), 7.60(d, 1H), 7.30(d, 1H), 7.20(d, 2H), 6.95(d, 1H), 6.80(d, 1H), 6.65(d, 2H), 4.65(t, 2H), 3.45(t, 2H), 3.20(m, 4H), 1.80(m, 6H)

Example 9
Step 1

Methanesulfonic acid 3-[4-(2-bromo-ethyl)-benzoyl]-2-(4-methanesulfonyloxy-phenyl)-benzo[b]thiophen-6-yl ester. A flask with 4-(2-Bromo-ethyl)-benzoic acid (190 mg) and thionyl chloride (0.5 mL) was heated to 50° C. for 3 hrs. The excess thionyl chloride was removed in vacuo. Methanesulfonic acid 2-(4-methanesulfonyloxy-phenyl)-benzo[b]thiophen-6-yl ester (290 mg) dissolved in 8 mL of methylene chloride was added to the residue along with triflic Acid (0.23 mL). The reaction was stirred at reflux for 16 hrs. The reaction mixture then was poured into cold sodium bicarbonate solution and the organic layer was separated, dried over anhydrous sodium sulfate, filtered, and concentrated. The crude product was chromatographed on silica gel using 1:10 Ethyl acetate/Hexanes to 2:3 Ethyl acetate/Hexanes as the gradient eluant to yield 174 mg of the title compound.

Step 2

Methanesulfonic acid 2-(4-methanesulfonyloxy-phenyl)-3-[4-(2-pyrrolidin-1-yl-ester)-benzoyl]-benzo[b]thiophen-6-yl ester. A solution of the product from Step 1, Example 9 (87 mg, 0.14 mmol) and pyrrolidine (100 mL) in 0.5 mL of Ethanol was heated to reflux for 16 hrs. The ethanol was evaporated off and the residue was diluted with water and extracted with methylene chloride. The organic layer was dried over anhydrous sodium sulfate, filtered, and concentrated. The crude product was chromatographed on silica gel using 5% diethylamine ethyl acetate as the eluant to obtain 38 mg of the title compound.

Step 3

[6-Hydroxy-2-(4-hydroxy-phenyl)-benzo[b]thiophen-3-yl]-[4-(2-pyrrolidin-1-yl-ethyl)-phenyl]-methanone. A solution of the product from Step 2, Example 9 (30 mg, 0.05 mmol) and 5N NaOH (0.076 mL) in 1.5 mL of ethanol was heated to reflux for 4 hrs. The solvent was stripped off and the residue was diluted with water and washed with ether. The aqueous layer was then acidified with 1N HCl, then the solution was adjusted to pH 9 with sodium bicarbonate solution at which time a precipitate was formed. The product was filtered off to give 18.3 mg of the title compound.

$^1$H NMR (DMSO-d$_6$) d 7.60(d, 2H), 7.35(d, 1H), 7.25(m, 3H), 7.15(d, 2H), 6.85(dd, 1H), 6.65(d, 2H), 2.75(bt, 2H), 2.40(m, 6H), 1.65(m, 4H)

Example 10
Step 1

Acetic acid 4-chlorocarbonyl-phenyl ester. A solution of 4-acetoxybenzoic acid (200 mg, 1.11 mmol), thionyl chloride(1.6 mL), 1 drop of DMF, and 7.5 mL of chlorobenzene was heated to 80° C. for 1.5 hrs. The reaction was then cooled to room temperature and the solvent and excess thionyl chloride were removed in vacuo. Theoretical yield of the title compound was assumed and the residue was used as is.

Step 2

Methanesulfonic acid 4-[3-(4-hydroxy-benzoyl)-6-methanesulfonyloxy -benzo[b]thiophen-2-yl]-phenyl ester. To a solution of methanesulfonic acid 4-(6-methanesulfonyloxy-benzo[b]thiophen-2-yl)-phenyl ester$^1$ (200 mg, 0.5 mmol) in 14 mL of methylene chloride was added the product from Step 1, Example 10 (104 mg, 0.53 mmol) and triflic acid (0.47 mL, 5.3 mmol). The reaction was stirred at reflux for 16 hrs, cooled to room temperature, and poured into saturated sodium bicarbonate solution and was extracted into methylene chloride. The organic layer was dried over anhydrous magnesium sulfate, filtered, and concentrated. The residue was purified by silica gel chromatography using 20% Ethyl acetate/ Hexanes to 50% Ethyl acetate/Hexanes as the gradient eluant to obtain 125 mg of the title compound.

Step 3

Methanesulfonic acid 4-{6-methanesulfonloxy-3-[4-(1-methyl-piperidin-2-ylmethoxy)-benzoyl]-benzo[b]thiophen-2-yl}-phenyl ester. A solution of the product from Step 2, Example 10 (115 mg, 0.22 mmol), (1-methyl-piperidin-2-yl)-methanol (28.7 mg, 0.22 mmol), and triphenylphosphine (75 mg, 0.29 mmol) in 3 mL of THF was cooled to 0° C. and diethyl azodicarboxylate (0.051 mL, 0.26 mmol) was added dropwise. After the addition was complete, the reaction was allowed to warm to room temperature and was stirred for 16 hrs. The THF was evaporated off and the residue was chromatographed on silica gel using 1% MeOH-1% Diethylamine-methylene chloride as the eluant to give 80 mg of the title compound.

Step 4

[6-Hydroxy-2-(4-hydroxy-phenyl)-benzo[b]thiophen-3-yl]-[4-(1-methyl -piperidin-3-ylmethoxy)-phenyl]-methanone. A solution of the product from Step 3, Example 10 (80 mg, 0.13 mmol) and 0.25 mL of 5N NaOH in 8 ml of ethanol was heated to reflux for 1 hr. The solvent was evaporated and the residue was diluted with water. The reaction was acidified with 3N HCl then made basic with saturated sodium bicarbonate solution. This aqueous solution was extracted with 1:2 MeOH/ methylene chloride. The combined organic layers were dried over anhydrous magnesium sulfate, filtered, and concentrated. The crude product was chromatographed on silica gel using 5% MeOH/CHCl$_3$ to 10% MeOH/CHCl$_3$ as the gradient eluant to obtain the title compound.

$^1$H NMR (MeOH-d$_4$) δ7.70(d, 2H), 7.40(d, 1H), 7.25(d, 1H), 7.15(d, 2H), 6.85(m, 3H), 6.60(d, 2H), 4.05(m, 2H), 2.95(m, 1H), 2.35(s, 3H), 2.30(m, 2H), 1.65(m, 6H).

Example 11

Step 1

Methanesufonic acid 4-{6-methansulfonyloxy-3-[4-(pyridin-2-ylmethoxy) -benzoyl]-benzo[b]thiophen-2-yl}-phenyl ester. The coupling of the product from Step 2, Example 10 (Methanesulfonic acid 4-[3-(4-hydroxy-benzoyl)-6-methanesulfonyloxy-benzo[b]thiophen-2-yl]-phenyl ester) and pyridin-2-yl-methanol was accomplished by using the procedure outlined in Example 10, Step 3 except stirring for 1 hour instead of 16 hours at room temperature. The solvent was evaporated off and the crude product was chromatographed on silica gel using 1% MeOH/methylene chloride to 2% MeOH/methylene chloride as the gradient eluant to yield the title compound.

Step 2

[6-Hydroxy-2-(4-hydroxy-phenyl)-benzo[b]thiophen-3-yl]-[4-(pyridin-2-yl -methoxy)-phenyl]-methanone. The mesylate protecting groups on the product from Step 1, Example 11 were removed as in Example 10, Step 4 to obtain the title compound.

$^1$H NMR (DMSO-d$_6$) δ8.55(d, 1H), 7.80(t, 1H), 7.65(d, 2H), 7.50(d, 1H), 7.35(m, 2H), 7.25(d, 1H), 7.15(d, 2H), 7.00(d, 2H), 6.85(dd, 1H), 6.65(d, 2H)

Example 12

Step 1

2-(4-Amino-phenylsulfanyl)-1-(4-methoxy-phenyl)-ethanone. To a mixture of 84 mL of ethanol and 33 mL of water was added 4.48 gm of potassium hydroxide and the mixture was stirred until all the potassium hydroxide was in solution. To this mixture was added 3-aminothiophenol (10.00 gm, 79.9 mmol) in one portion. The reaction was cooled to 5° C. and a solution of 2-bromo-4-methoxyacetophenone (18.0 gm, 79.9 mmol) in 30 mL of ethyl acetate was slowly added. The reaction was stirred vigorously for 1 hr. keeping the temperature below 23° C. The solvent was evaporated off and the residue was back extracted into ethyl acetate.from water. The aqueous layer was extracted with ethyl acetate. The combined organic layers were then dried over anhydrous magnesium sulfate, filtered, and concentrated. The solid residue was recrystallized from ethanol to yield 16.9 gm of the title compound.

Step 2

N-{4-[2-(4-Methoxy-phenyl)-2-oxo-ethylsufanyl]-phenyl}-acetamide. A solution of the product from Step 1, Example 12 (2.00 gm, 7.33 mmol), pyridine (1.78 mL, 21.9 mmol), 4-dimethylaminopyridine (859 mg, 7.33 mmol) and acetic anhydride (0.83 mL, 8.79 mmol) in 9 mL of methylene chloride was stirred at room temperature for 2 hrs. The reaction was diluted with methylene chloride and washed with water, 1N HCl, and water again. The organic layer was dried over anhydrous sodium sulfate, filtered, and concentrated. The crude product was recrystallized from ethyl acetate to obtain 1.17 gm of the title compound.

Step 3

N-[2-(4-Methoxy-phenyl)-benzo[b]thiophen-6-yl]-acetamide. A flask containing polyphosphoric acid (6.4 gm) was heated on a steam bath to 90° C. and to this was added the product from Step 2, Example 12 (1.17 gm, 3.73 mmol) portionwise. The reaction mixture turned black and was stirred at 90° C. for 4.5 hrs. The reaction was then cooled to about 70° C. and poured into vigorously stirring ice-water water mixture. The crude product precipitated out and was collected by vacuum filtration, washing well with water. The material was pumped dry under vacuum and was slurried in refluxing acetone for 1 hr., cooled, filtered, washed with acetone, and pumped dry to yield the title compound.

Step 4

N-{2-(4-Hydroxy-phenyl)-3-[4-(2-piperidin-1-yl-ethoxy)-benzoyl]-benzo[b]thiophen-6-yl}-acetamide. To a solution of the product from Step 3, Example 12 (1.8 gm, 6.08 mmol) and 4-(2-piperidin-1-yl-ethoxy)-benzoyl chloride$^1$ (7.29 mmol) in 65 mL of methylene chloride was added, in three portions, aluminum trichloride (6.08 gm, 46 mmol) keeping the internal temperature at 28° C. The reaction was stirred at this temperature for 3 hrs. Acylation was complete, then the methyl protecting group was removed by the dropwise addition of ethanethiol (2.0 mL, 26.7 mmol) and stirring for 3 hrs at room temperature. The reaction was then cooled to 0° C. and was quenched by dropwise addition of 41 mL of THF, 20% HCl (6.66 mL), and 41 mL of water keeping the temperature around 5° C. A gummy solid was produced after the reaction was quenched which was then filtered from the solvents. The solids were dissolved in MeOH, diluted with Ethyl acetate, and washed with saturated sodium bicarbonate solution. A precipitate formed and was removed by filtration. The filtrate layers were separated and the aqueous layer was extracted again with ethyl acetate. The organic layers were combined, dried over anhydrous sodium sulfate, filtered, and concentrated. Alternatively the reaction can be quenched with saturated sodium bicarbonate solution followed by extraction with a mixture of 2:1 chloroform-methanol. The aluminum salts are filtered off through a pad of Celite then the layers of the filtrate are separated. The aqueous layer is extracted with chloroform-methanol. The combined organic layers is washed with brine, dried over anhydrous magnesium sulfate, filtered and concentrated. The crude material was chromatographed on silica gel using 5% MeOH:methylene chloride as the eluant to obtain 500 mg of the title compound.

$^1$H NMR (MeOH-d$_4$) δ8.45(d, 1H), 7.75(d, 2H), 7.60(d, 1H), 7.40(dd, 1H), 7.25(d, 2H), 6.90(d, 2H), 6.65(d, 2H), 4.15(t, 2H), 2.85(t, 2H), 2.60(m, 4H), 2.20(s, 3H), 1.65(m, 4H), 1.50(m, 2H)

Example 13

Step 1

[6-Amino-2-(4-hydroxy-phenyl)-benzo[b]thiophen-3-yl]-[4-(2-piperidin-1-yl -ethoxy)-phenyl]-methanone. A solution of the product from Step 4, Example 12 (400 mg, 0.78 mmol) and 2.4 mL of 5N NaOH in 24 mL of ethanol was stirred at reflux for 48 hrs. The ethanol was evaporated off and the residue was diluted with water and acidified with 1N HCl to pH3. The aqueous solution was then made basic with saturated sodium bicarbonate solution. A solid precipitated and was filtered to yield the title compound.

$^1$H NMR (MeOH-d4) δ7.75(d, 2H), 7.35(d, 1H), 7.20(m, 3H), 6.90(d, 2H), 6.85(dd, 1H), 6.60(d, 2H), 4.20(t, 2H), 2.95(t, 2H), 2.70(m, 4H), 1.70(m, 4H), 1.55(m, 2H)

Example 14

Step 1

N-{2-(4-Hydroxy-phenyl)-3-[4-(2-piperidin-1-yl-ethoxy)-benzoyl]-benzo[b]-thiophen-6-yl}-formamide. Formic acid (0.18 mL, 4.57 mmol) was added dropwise to a flask containing acetic anhydride (0.36 mL, 3.84 mmol) at 0° C. The mixture was then heated for 2 hrs. at 50° C. At this time the mixture was cooled to room temperature and 0.29 mL of THF was added. In a separate flask the product from Step 1, Example 13 (150 mg, 3.17 mmol) was suspended in 1.2 mL of THF and cooled to −20° C. To this suspension was added the acetic formic anhydride solution (0.088 mL). The reaction was stirred for 2 hrs. then was concentrated to dryness and pumped dry under high vacuum. The crude product was chromatographed in silica gel using 7%

MeOH:0.5% NH$_4$OH:methylene chloride as the eluant to obtain 65 mg of the title compound.

$^1$H NMR (MeOH-d$_4$) δ8.45(s, 1H), 8.40(s, 1H), 7.75(d, 2H), 7.60(d, 1H), 7.40(dd, 1H), 7.25(d, 2H), 6.90(d, 2H), 6.70(d, 2H), 4.15(t, 2H), 2.80(t, 2H), 2.55(m, 4H), 1.65(m, 4H), 1.50(m, 2H)

Example 15

Step 1

N-{2-(4-Hydroxy-phenyl)-3-[4-(2-piperidin-1-yl-ethoxy)-benzoyl]-benzo[b]-thiophen-6-yl}-methanesulfonamide. The product from Step 1, Example 14 was reacted with methanesulfonyl chloride (1.1 equivalent) in methylene chloride with 1 equivalent of 4-dimethylaminopyridine and 2 equivalents of triethylamine. When finished the reaction was concentrated and chromatographed on silica gel to obtain the title compound.

$^1$H NMR (MeOH-d$_4$) δ7.90(d, 1H), 7.75(d, 2H), 7.60(d, 1H), 7.25(m, 3H), 6.90(d, 2H), 6.65(d, 2H), 4.20(t, 2H), 3.05(s, 3H), 2.95(t, 2H), 2.70(m, 4H), 1.70-(m, 4H), 1.55(m, 2H)

Example 16

Step 1

1-(2,2-Diethoxy-ethylsulfanyl)-3-methoxy-benzene. To a solution of 3-methoxybenzenethiol (15.0 mL, 120 mmol) and potassium carbonate (16.6 gm, 120 mmol) in 150 mL of acetone at room temperature was added dropwise 2-bromo-1,1-diethoxy-ethane (16.5 mL, 110 mmol). The reaction mixture was stirred at room temperature for 16 hours. The solids in the reaction mixture were removed by filtration and were washed well with acetone. The filtrate was concentrated. The residue was diluted with water and extracted several times with ether. The ether layers were combined and washed with 0.5 M KOH, water, brine, and were then dried over anhydrous sodium sulfate, filtered, and concentrated to yield 28.2 gm of the title compound.

Step 2

6-Methoxy-benzo[b]thiophene. To a solution of boron trifluoride etherate (14.45 mL, 115 mmol) in 2000 mL of methylene chloride stirring in a cold water bath 20° C. was added dropwise 1-(2,2-Diethoxy-ethylsulfanyl)-3-methoxy-benzene (28.2 gm, 110 mmol) dissolved in 500 mL of methylene chloride. The addition was complete in 3 hrs. and then the reaction was warmed to room temperature for a further 1.5 hrs. The reaction mixture was then quenched with saturated sodium bicarbonate solution. The organic layer was separated and the aqueous layer was back extracted several times with methylene chloride. The organic layers were combined, dried over anhydrous sodium sulfate, filtered, and concentrated. The crude product was chromatographed on silica gel (using a gravity column) using hexanes as the eluant to yield 10.9 gm of the title compound.

General Procedure for the Synthesis of Compunds of Formula IV

The general scheme is outlined in Scheme 8b. Three sets of conditions are used for the acylation step and they are described below. Table 2 lists the compounds with relevant data and which procedure was used in each case.

Step 3

6-Methoxy-2-phenyl-benzo[b]thiophene. To a solution of 6-Methoxy -benzo[b]thiophene (250 mg, 1.52 mmol) in 3.7 mL THF at −20° C. was added dropwise n-butyllithium (0.67 mL, 1.67 mmol). The mixture was stirred at 0° C. for 1.5 hrs. and at room temperature for 0.5 hrs. Anhydrous zinc chloride (269 mg, 1.97 mmol) in 1.9 mL of THF was added by cannula to the reaction. The reaction was then stirred at room temperature for 15 minutes and then Pd(Ph$_3$P)$_4$ (70 mg, 0.06 mmol) and iodobenzene (0.22 mL, 1.97 mmol) were added and the reaction stirred at room temperature for 3 hrs. Other aromatic or heteroaromatic bromides, iodides or triflates can replace iodobenzene in this procedure. If a triflate is used 3 equivalents of anhydrous lithium chloride must be added. The reaction can be refluxed overnight to push it towards completion. The solvent was evaporated and the residue was diluted water and extracted into ethyl acetate. The combined organic layers was dried over anhydrous sodium sulfate, filtered, and concentrated. The crude product was chromatographed on silica gel using 100% Hexanes to 1% ethyl acetate/hexanes as the gradient eluant to yield 250 mg of the title compound.

Acylation Procedure A

Step 4

(6-Hydroxy-2-phenyl-benzo[b]thiophen-3-yl)-[4-(2-piperidin-1-yl-ethoxy) -phenyl]-methanone. A solution of the product from Step 3, Example 16 (272 mg, 1.13 mmol), 4-(2-Piperidin-1-yl-ethoxy)-benzoyl chloride (7.9 mL, 1.53 mmol), and titanium tetrachloride (6.62 mL, 5.66 mmol) in 16.5 mL of methylene chloride was stirred at room temperature for 6 hrs. To demethylate, ethanethiol (0.335 mL, 4.53 mmol) and AlCl$_3$ (600 mg, 4.53 mmol) in two portions were added to the reaction and it was stirred for an additional 2.5 hrs. The reaction was quenched with saturated sodium bicarbonate solution and the solution was extracted twice with methylene chloride. The organic layers were combined, dried over anhydrous sodium sulfate, filtered, and concentrated. The crude product was chromatographed on silica gel using 1% MeOH: CH$_2$Cl$_2$ to 5% MeOH CH$_2$Cl$_2$ as the gradient eluant to obtain 231 mg of the title compound.

$^1$H NMR (MeOH-d$_4$) δ7.70(d, 2H), 7.40(m, 3H), 7.30(d, 1H), 7.25(m, 3H), 6.90(d, 1H), 6.85(d, 2H), 4.15(t, 2H), 2.75(t, 2H), 2.55(m, 4H), 1.60(m, 4H), 1.50(m, 2H)

Example 17

Step 1

2-(4-Fluoro-phenyl)-6-methoxy-benzo[b]thiophene. The reaction of (250 mg, 1.52 mmol) and 4-Fluoroiodobenzene (0.228 mL, 1.5 mmol) was performed as in Example 16, Step 3. The crude product was chromatographed on silica gel using Hexanes as the eluant to give 280 mg of the title compound.

Acylation Procedure B

Step 2

{2-(4-Fluoro-phenyl)-6-hydroxy-benzo[b]thiophen-3-yl]-[4-(2-piperidin-1-yl-ethoxy)-phenyl]-methanone. To a solution of the product from Example 17, Step 1 (83 mg, 0.32 mmol) and 4-(2-Piperidin-1-yl-ethoxy)-benzoyl chloride (1.39 mL, 0.39 mmol) in 3.3 mL of 1,2-dichloroethane was added, in two portions, aluminum trichloride (322 mg, 2.4 mmol) and the reaction was heated at reflux for 1 hr. At this time the coupling was complete and demethylation was carried out cooling the reaction to room temperature, adding ethanethiol (0.10 mL, 1.41 mmol) dropwise and stirring at room temperature for a further 1.5 hrs. The reaction was quenched with saturated sodium bicarbonate solution and extracted twice with methylene chloride. The organic layers were combined, dried over anhydrous sodium sulfate, filtered, and concentrated. The crude material was chromatographed on silica gel using 1% MeOH:methylene chloride to 3% MeOH:methylene chloride as the gradient eluant to yield the title compound.

$^1$H NMR (MeOH-d$_4$) δ7.75(d, 2H), 7.45(m, 3H), 7.35(d, 1H), 7.05(d, 2H), 6.95(dd, 1H), 6.90(d, 2H), 4.20(t, 2H), 2.80(t, 3H), 2.60(m, 4H), 1.65(m, 4H), 1.50(m, 2H)

Example 18

Step 1

Trifluoro-methanesulfonic acid benzothiazol-6-yl ester. To a suspension of 6-Hydroxybenzothiazole (1.00 gm, 6.61 mmol) in 30 mL of methylene chloride,at −78° C. was added triethylamine (2.76 mL, 19.8 mmol) and 4-dimethylaminopyridine (800 mg, 6.5 mmol) then trifluoromethanesulfonic anhydride (1.33 mL, 7.9 mmol). The reaction was allowed to warm to room temperature and stirred for 1 hr. The reaction was then quenched with saturated sodium bicarbonate solution and extracted into methylene chloride. The organics were combined, dried over anhydrous sodium sulfate, filtered, and concentrated. The crude product was chromatographed on silica gel using 1:10 Ethyl acetate/Hexanes to 1:4 Ethyl acetate/Hexanes as the gradient eluant to yield 1.41 gm of the title compound.

Step 2

6-(6-Methoxy-benzo[b]thiophen-2-yl)-benzothiazole. A solution of 6-methoxybenzo[b]thiophene (300 mg, 1.82 mmol) in 5 mL of THF was cooled to −20° C. and 2.5 M n-BuLi (0.8 mL, 2.01 mmol) was added dropwise. The reaction was stirred at 0° C. for 0.5 hrs and then warmed to room temperature for an additional 0.5 hrs. Next a 0.5 M solution of anhydrous zinc chloride in THF (4.75 mL, 2.38 mmol) was added and the reaction was stirred at room temperature for 15 minutes followed by the addition of anhydrous lithium chloride (3 equivalents), tetrakis-triphenylphosphine palladium (84 mg, 0.073 mmol) and, by cannula, the product from Example 18, Step 1 (505 mg, 2.01 mmol) dissolved in 2 mL of THF. The reaction was stirred at room temperature for 16 hrs. The THF was removed and the residue diluted in water and extracted three times with Ethyl acetate. The combined organics were dried over anhydrous sodium sulfate, filtered, and concentrated. The crude material was chromatographed on silica gel using 1:20 THF/Hexanes to 1:10 THF/Hexanes as the gradient eluant to yield the title compound.

Acylation Procedure C

Step 3

(2-Benzothiazol-6-yl-6-hydroxy-benzo[b]thiophen-3-yl)-[4-(2-piperidin-1-yl -ethoxy)-phenyl]-methanone. To a solution of the product from Example 18, Step 2 (63 mg, 0.21 mmol) and 4-(2-Piperidin-1-yl-ethoxy)-benzoyl chloride (1.38 mL, 0.25 mmol) in 1 mL of methylene chloride was added AlCl$_3$ (212 mg, 1.6 mmol) and the reaction was stirred at room temperature for 3 hrs. When acylation was complete, to demethylate, ethanethiol (0.069 mL, 0.93 mmol) was added dropwise and the reaction stirred for a further 1.5 hrs. The reaction was cooled to 0° C. and quenched with saturated sodium bicarbonate solution. The organic layer was separated and the aqueous layer was extracted with 10% MeOH/methylene chloride. The organic layers were combined, dried over anhydrous sodium sulfate, filtered, and concentrated. The crude product was chromatographed on silica gel using 2% MeOH/methylene chloride to 4% MeOH/methylene chloride as the gradient eluant to obtain the title product.

$^1$H NMR (MeOH-d$_4$) δ9.20(s, 1H), 8.10(s, 1H), 7.90(d, 1H), 7.70(d, 2H), 7.55(d, 1H), 7.50(d, 1H), 7.30(d, 1H), 6.95(d, 1H), 6.80(d, 2H), 4.10(t, 2H), 2.70(t, 2H), 2.50(m, 4H), 1.60(m, 4H), 1.45(m, 2H)

Example 19

Step 1

2-Cyclohex-1-enyl-6-methoxy-benzo[b]thiophene. To a solution of 6-methoxybenzo[b]thiophene (362 mg, 2.21 mmol) in 5.5 mL of THF at −20° C. was added dropwise 2.5 M nBuLi (0.97 mL, 2.4 mmol) and the reaction was stirred at 0° C. for 40 minutes and was then warmed to room temperature for 30 minutes. Next, ZnCl$_2$ (390 mg, 2.87 mmol) in 2.5 mL of THF was added by cannula and the reaction was stirred at room temperature for 15 minutes. At this point, Pd(Ph$_3$P)$_4$ (102 mg), trifluoromethanesulfonic acid cyclohex-1-enyl ester (0.6 gm, 2.93 mmol)$^3$ and anhydrous lithium chloride (0.28 gm, 6.63 mmol) were added and then the reaction mixture was stirred for 16 hrs. at room temperature. The tetrahydrofuran was removed in vacuo and the residue diluted with water and extracted with ethyl acetate. The combined organic layers was dried over anhydrous sodium sulfate, filtered, and concentrated. The crude product was chromatographed on silica gel using hexanes as the eluant to yield 368 mg of the title compound.

3. *Tetrahedron Letters* 1983, Vol 24, 979

Step 2

2-Cyclohexyl-6-methoxy-benzo[b]thiophene. The product from Example 19, Step 1 (264 mg) and 10% Palladium on Carbon (60 mg) in 30 mL of ethyl acetate was added to a Parr shaker flask and hydrogenated at 50 psi for 16 hrs. at room temperature. The mixture was filtered over celite and concentrated. The crude product was chromatographed on silica gel using Hexanes as the eluant to give 210 mg of the title compound.

Step 3

(2-Cyclohexyl-6-hydroxy-benzo[b]thiophen-3-yl)-[4-(2-piperidin-1-yl -ethoxy)-phenyl]-methanone. The product from Example 19, Step 2 and 4-(2-Piperidin-1-yl-ethoxy)-benzoyl chloride were coupled according to procedure C above and the methyl protecting group removed using etanethiol/aluminum trichloride to yield the title compound.

$^1$H NMR (MeOH-d$_4$) δ7.85(d, 2H), 7.25(d, 1H), 7.15(d, 1H), 7.10(d, 2H), 6.80(d, 1H), 4.25(t, 2H), 2.85(t, 2H), 2.65(m, 4H), 2.00(m, 2H), 1.65(m, 1H), 1.30(m, 3H).

Example 20

Step 1

[6-Methoxy-2-(4-methoxy-phenyl)-benzo[b]thiophen-3-yl]-(4-methoxy -phenyl)-methanone. To a suspension of 6-methoxy-2-(4-methoxyphenyl) -benzo[b]thiophene (2 g, 7.4 mmol), and ρ-anisoyl chloride in 110 mL of methylene chloride was added aluminum trichloride (4.93 g, 37 mmol) in three portions and the reaction was stirred overnight. It was then quenched with 200 mL of 2N sodium hydroxide and extracted with methylene chloride. The combined organic layers was washed with brine and dried over anhydrous magnesium sulfate. After filtration, concentration and silica gel column chromatography using 15% ethyl acetate—hexanes as eluant the title compound (1.73 g) was obtained.

Step 2

[6-Methoxy-2-(4-methoxy-phenyl)-benzo[b]thiophen-3-yl]-(4-hydroxy-phenyl)-methanone. To a solution of ethanethiol (538 mL, 7.27 mmol) in 1.88 mL of tetrahydrofuran, cooled to −30° C. was added n-butyllithium (2.57 mL, 2.5 M, 6.42 mmol) and the reaction was warmed to room temperature. Dimethylformamide (1 mL) was added then the product from Step 1 (1.73 g, 4.3 mmol) in 2.7 mL of dimethylformamide. The reaction was heated at 58° C. for two hours then at 80° C. for 1 hour. The cooled reaction was poured into 33 mL oh 1N hydrochloric acid and extracted with ethyl acetate. The combined organic layers was washed with brine and dried over anhydrous magnesium sulfate. After filtration, concentration and silica gel column chromatography using 15% ethyl acetate -hexanes as eluant the title compound (1.17 g) was obtained.

¹H NMR (CDCl₃) δ7.7 (d, 2H), 7.55 (d, 1H), 7.36 (d, 2H), 7.31 (d, 1H), 6.95 (dd, 1H), 6.76 (d, 2H), 6.68 (d, 2H), 3.9 (s, 3H), 3.75 (s, 3H)

Step 3

[4-(1-Benzyl-piperidine-2-ylmethoxy)-phenyl]-[6-methoxy-2-(4-methoxy -phenyl)-benzo[b]thiophen-3-yl]-methanone. The product from Step 2 (600 mg) was coupled with (1-benzyl-piperidin-2-yl)-methanol (379 mg) as is Example 10, Step 3 to yield the title compound (320 mg) after silica gel chromatography with 10% ethyl acetate/hexanes to 20% ethyl acetate/hexanes as the gradient eluant.

Step 4

[4-(1-Benzyl-piperidine-2-ylmethoxy)-phenyl]-[6-hydroxy-2-(4-hydroxy -phenyl)-benzo[b]thiophen-3-yl]-methanone. The product from Step 3 (295 mg, 0.5 mmol) was combined with boron tribromide (2.50 mL, 1M in dichloromethane, 2.5 mmol) in 4 mL of methylene chloride at room temperature. After 2 hours the reaction was quenched with saturated sodium bicarbonate solution and extracted into chloroform-methanol (10: 1). The combined organic layers was washed with brine and dried over anhydrous magnesium sulfate. After filtration, concentration and silica gel column chromatography with 40% ethyl acetate-hexanes as eluant the title compound (169 mg) was obtained.

Step 5

[6-Hydroxy-2-(4-hydroxy-phenyl)-benzo[b]thiophen-3-yl]-(4-piperidine-2-ylmethoxy)-phenyl)-methanone. The product from Step 4 (165 mg) was dissolved in 25 mL of ethanol and 6 mL of acetic acid and hydrogenated at 50 psi with 100 mg of 10% palladium on carbon as catalyst for 3 hours. The catalyst was removed by filtration through a pad of Celite and the filtrate was concentrated. The acetic acid was removed by azeotroping with heptane. The product was purified by silica gel chromatography with 5% methanol-methylene chloride as eluant.

¹H-NMR (MeOH-d₄) δ7.66 (d, 2H), 7.4 (d, 1H), 7.25 (d, 1H), 7.1 (d, 2H), 6.8 (dd, 1H), 6.78 (d, 2H), 6.6 (d, 2H)3.9 (dd, 1H), 3.75 (dd, 1H), 3.1 (bd, 1H), 2.95 (m, 1H), 2.6 (m, 1H), 1.2–1.9 (m)

Step 6

[6-Hydroxy-2-(4-hydroxy-phenyl)-benzo[b]thiophen-3-yl]-[4-(1-ethyl-piperidin-3-ylmethoxy)-phenyl]-methanone. The product from Step 5 (19 mg, 0.04 mmol) was combined with acetaldehyde (10 mL), sodium cyanoborohydride (4 mg, 0.062 mmol) in 200 mL of methanol and the whole was stirred at room temperature overnight. The reaction was diluted with water and extracted with 2:1 methylene chloride/methanol. The combined organic layers was washed with brine and dried over anhydrous magnesium sulfate. After filtration, concentration and silica gel column chromatography with 5% methanol-methylene chloride-2% aqueous ammonium hydroxide as eluant the title compound (3 mg) was obtained.

¹H NMR (MeOH-d₄) δ7.7 (d, 2H), 7.4 (d, 1H), 7.25 (d, 1H), 7.15 (d, 2H), 6.35 (dd, 1H), 6.3 (d, 2H), 6.6 (d, 2H), 4.05 (d, 2H), 1.06 (t, 3H)

Example 21

Step 1

(4-Iodo-phenyl)-[6-methoxy-2-(4-methoxy-phenyl)-benzo[b]thiophen-3-yl]-methanone. To a suspension of 6-methoxy-2-(4-methoxyphenyl)-benzo[b]thiophene 25 (3 g, 11.1 mmol), and ρ-iodobenzoyl chloride in 65 mL of methylene chloride was added aluminum trichloride (2.1 g) in three portions and the reaction was stirred 3 hours. It was then poured into ice-water and extracted with methylene chloride. The combined organic layers was washed with brine and dried over anhydrous magnesium sulfate. After filtration, concentration and silica gel column chromatography with 3% ethyl acetate-hexanes as eluant the title compound (3.97 g) was obtained.

¹H-NMR (CDCl₃) δ7.6 (d, 2H), 7.6 (d, 1H), 7.45 (d, 2H), 7.32 (d, 1H), 7.0 (dd, 1H), 6.78 (d, 2H), 3.9 (s, 3H), 3.78 (s, 3H)

Step 2

[4-(3-Hydroxy-prop-1-ynyl)-phenyl]-[6-methoxy-2-(4-methoxy-phenyl) -benzo[b]-thiophen-3-yl]-methanone. The product from Step 1 (214 mg, 0.43 mmol) was combined with triethylamine (35 mL), copper (I) iodide (0.4 mg), propargyl alcohol (50 mL, 0.86 mmol), bis-triphenylphosphine palladium dichloride at room temperature. The copper iodide was added last. The reaction was stirred for 3 hours then diluted with water and extracted into methylene chloride. The combined organic layers was dried over anhydrous magnesium sulfate. After filtration, concentration and silica gel column chromatography with 1.5% methanol-methylene chloride (gravity column) as eluant the title compound (195 mg) was obtained.

Step 3

Methanesulfonic acid 3-{4-[6-methoxy-2-(4-methoxy-phenyl) -benzo[b]thiophene-3-carbonyl]-phenyl}-prop-2-ynyl ester. The product from Step 2 (195 mg, 0.46 mmol) was dissolved in 3 mL of methylene chloride and treated with 127 mL of triethylamine and methanesulfonyl chloride (53 mL, 0.68 mmol) and stirred 30 minutes at room temperature. The reaction was concentrated and extracted into ethyl acetate. The combined organic layers was washed with brine and dried over anhydrous magnesium sulfate. After filtration, concentration the title compound (205 mg) was obtained.

Step 4

[6-Methoxy-2-(4-methoxy-phenyl)-benzo[b]thiophen-3-yl]-[4-(3-piperidin-1-yl-prop-1-ynyl)-phenyl]-methanone. The product from Step 3 (205 mg, 0.4 mmol) was combined with cesium carbonate (197 mg, 0.6 mmol), piperidine (44 mL, 0.44 mmol) in dimethylformamide at room temperature. After four hours the reaction was diluted with ethyl acetate and washed with water and brine. The organic layer was dried over anhydrous magnesium sulfate. After filtration, concentration the title compound (120 mg) was obtained.

Step 5

[6-Hydroxy-2-(4-hydroxy-phenyl)-benzo[b]thiophen-3-yl]-[4-(3-piperidin-1-yl-prop-1-ynyl)-phenyl]-methanone. The product from Step 4 (120 mg, 0.24 mmol) was dissolved in methylene chloride (0.5 mL), cooled to 0° C. and treated with boron tribromide (1.2 mL, 1 M, 1.2 mmol) and stirred for 30 minutes. The reaction was quenched with saturated sodium bicarbonate solution and extracted intochloroform. The combined organic layers was dried over anhydrous magnesium sulfate. After filtration, concentration and silica gel column chromatography with 2% methanol-methylene chloride as eluant the title compound (24 mg) was obtained.

¹H-NMR (MeOH-d₄) d 7.6 (d, 2H), 7.5 (d, 1H), 7.28 (d, 2H), 7.25 (d, 1H), 7.1 (d, 2H), 6.88 (dd, 1H), 6.58 (d, 2H), 3.45 (s, 2H), 2.57 (m, 4H), 1.62 (m, 4H), 1.5 (m, 2H)

TABLE 1

[Core structure: 6-hydroxy-2-(4-hydroxyphenyl)benzo[b]thiophen-3-yl 4-(2-X-ethoxy)phenyl ketone]

| X = | DATA |
|---|---|
| (8-azabicyclic amine, N-linked) | ¹H-NMR(CDCl₃) 7.70(d, 2H), 7.25(m, 6H), 6.60(d, 1H), 6.55(d, 2H), 4.10(t, 2H), 2.90(t, 2H), 2.75(d, 4H), 1.90(bm, 2H), 1.75(bm, 4H), 1.60(bm, 4H) |
| (trans-decahydroisoquinolin-2-yl) | Mass Spectroscopy - M + 1 = 529 R_f = 0.51 (9:1 Chloroform/Methanol) |
| (1,2,3,4-tetrahydroisoquinolin-2-yl) | ¹H-NMR(CD₃OD) 7.75(d, 2H), 7.45(d, 1H), 7.30(d, 1H), 7.25(m, 2H), 7.15(d, 2H), 7.10(m, 2H), 6.92(d, 2H), 6.90(d, 1H), 6.70(d, 2H), 4.30(t, 2H), 3.75(s, 2H), 3.00(t, 2H), 2.95(m, 4H) |
| (4-dimethylaminopiperidin-1-yl) | ¹H-NMR (CD₃OD) 7.75(d, 2H), 7.45(d, 1H), 7.30(d, 1H), 7.20(d, 2H), 6.85(m, 3H), 6.65(d, 2H), 4.15(t, 2H), 3.15(bd, 2H), 2.80(t, 2H), 2.40(s, 6H), 2.20(bt, 2H), 1.95(bd, 2H), 1.65(bt, 2H) |
| (4-methylpiperazin-1-yl) | ¹H-NMR (DMSO-d6) 9.75(bm, 2H), 7.65(d, 2H), 7.35(d, 1H), 7.25(d, 1H), 7.15(d, 2H), 6.95(d, 2H), 6.85(dd, 1H), 6.65(d, 2H), 4.10(t, 2H), 2.65(t, 2H), 2.40(bm, 4H), 2.30(bm, 4H), 2.20(s, 3H) |
| (4-oxopiperidin-1-yl / 4,4-dihydroxypiperidin-1-yl equilibrium) | ¹H-NMR (CD₃OD) 7.75(d, 2H), 7.45(d, 1H), 7.35(d, 1H), 7.20(d, 2H), 6.85(m, 3H), 6.65(d, 2H), 4.15(bt, 2H), 2.95(bm, 4H), 2.65(bt, 2H), 2.50(t, 2H), 1.80(bt, 2H) |
| (norbornylamino, NH) | ¹H-NMR (CD₃OD) 7.70(d, 2H), 7.40(d, 1H), 7.25(d, 1H), 7.15(d, 2H), 6.80(m, 3H), 6.60(d, 2H), 4.10(t, 2H), 3.00(m, 2H), 2.65(m, 1H), 2.20(bt, 2H), 1.35(bm, 8H) |
| (1,2,4-triazol-1-yl) | ¹H-NMR (CD₃OD) 8.50(s, 1H), 7.95(s, 1H), 7.70(d, 2H), 7.20(d, 1H), 6.90(m, 3H), 6.75(d, 2H), 6.65(dd, 1H), 6.40(d, 2H), 4.60(t, 2H), 4.30(t, 2H) |
| (methyl-aryl-substituted azabicyclic amine) | ¹H-NMR (CDCl₃) 7.65(d, 2H), 7.45(d, 1H), 7.19(d, 1H), 7.10(m, 6H), 6.80(dd, 1H), 6.60(d, 2H), 6.55(d, 2H), 4.05(bt, 2H), 3.50(d, 1H), 3.25(d, 1H), 2.95(bt, 2H), 2.75(d, 1H), 2.70(dd, 1H), 2.30(s, 3H), 1.70(m, 1H), 1.35(m, 1H), 0.80(m, 1H) |
| (imidazol-1-yl) | ¹H-NMR (CD₃OD) 7.75(m, 3H), 7.45(d, 1H), 7.29(d, 1H), 7.20(d, 1H), 7.18(d, 2H), 7.00(s, 1H), 6.85(m, 3H), 6.60(d, 2H), 4.40(t, 2H), 4.30(t, 2H) |
| (methyl-azabicyclic amine) | Mass Spectroscopy - M + 1 = 500 R_f = 0.64 (9:1 Chloroform/Methanol) |
| —OH | Mass Spectroscopy - M = 406 R_f = 0.50 (9:1 Chloroform/Methanol) |
| (cyclopropylamino, NH) | Mass Spec 446 (M + 1), 391 |
| (azabicyclic amine) | ¹H-NMR (CD₃OD) 7.85(d, 2H), 7.57(d, 1H), 7.35(d, 1H), 7.29(d, 2H), 7.05(d, 2H), 7.03(dd, 1H), 6.78 (d, 2H), 4.45 (t, 2H), Mass Spec 486 (M + 1) |
| (thiomorpholin-4-yl) | Mass Spec M⁺ 492 Tlc: R_f = 0.4 (9:1 Chloroform-Methanol) |

TABLE 2

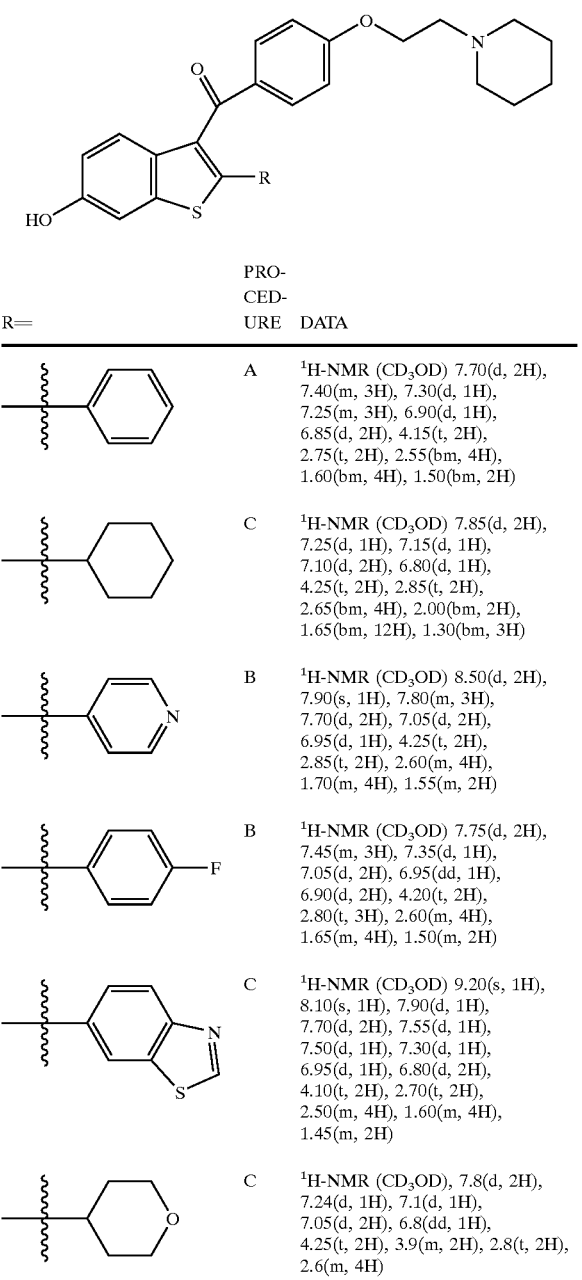

| R= | PROCEDURE | DATA |
|---|---|---|
| phenyl | A | $^1$H-NMR (CD$_3$OD) 7.70(d, 2H), 7.40(m, 3H), 7.30(d, 1H), 7.25(m, 3H), 6.90(d, 1H), 6.85(d, 2H), 4.15(t, 2H), 2.75(t, 2H), 2.55(bm, 4H), 1.60(bm, 4H), 1.50(bm, 2H) |
| cyclohexyl | C | $^1$H-NMR (CD$_3$OD) 7.85(d, 2H), 7.25(d, 1H), 7.15(d, 1H), 7.10(d, 2H), 6.80(d, 1H), 4.25(t, 2H), 2.85(t, 2H), 2.65(bm, 4H), 2.00(bm, 2H), 1.65(bm, 12H), 1.30(bm, 3H) |
| 4-pyridyl | B | $^1$H-NMR (CD$_3$OD) 8.50(d, 2H), 7.90(s, 1H), 7.80(m, 3H), 7.70(d, 2H), 7.05(d, 2H), 6.95(d, 1H), 4.25(t, 2H), 2.85(t, 2H), 2.60(m, 4H), 1.70(m, 4H), 1.55(m, 2H) |
| 4-fluorophenyl | B | $^1$H-NMR (CD$_3$OD) 7.75(d, 2H), 7.45(m, 3H), 7.35(d, 1H), 7.05(d, 2H), 6.95(dd, 1H), 6.90(d, 2H), 4.20(t, 2H), 2.80(t, 2H), 2.60(m, 4H), 1.65(m, 4H), 1.50(m, 2H) |
| benzothiazolyl | C | $^1$H-NMR (CD$_3$OD) 9.20(s, 1H), 8.10(s, 1H), 7.90(d, 1H), 7.70(d, 2H), 7.55(d, 1H), 7.50(d, 1H), 7.30(d, 1H), 6.95(d, 1H), 6.80(d, 2H), 4.10(t, 2H), 2.70(t, 2H), 2.50(m, 4H), 1.60(m, 4H), 1.45(m, 2H) |
| tetrahydropyranyl | C | $^1$H-NMR (CD$_3$OD), 7.8(d, 2H), 7.24(d, 1H), 7.1(d, 1H), 7.05(d, 2H), 6.8(dd, 1H), 4.25(t, 2H), 3.9(m, 2H), 2.8(t, 2H), 2.6(m, 4H) |

TABLE 2-continued

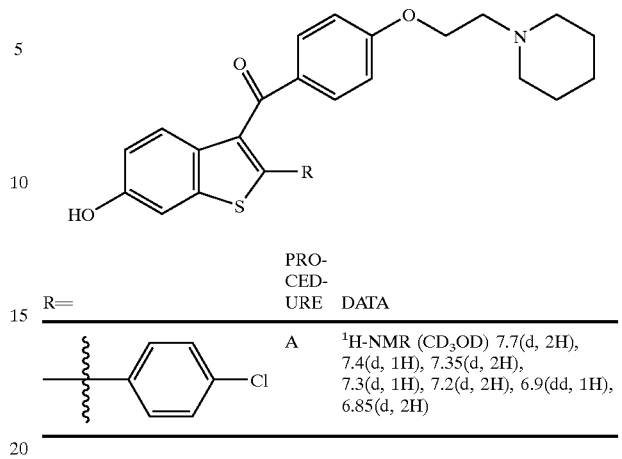

| R= | PROCEDURE | DATA |
|---|---|---|
| 4-chlorophenyl | A | $^1$H-NMR (CD$_3$OD) 7.7(d, 2H), 7.4(d, 1H), 7.35(d, 2H), 7.3(d, 1H), 7.2(d, 2H), 6.9(dd, 1H), 6.85(d, 2H) |

What is claimed is:

1. A compound of Formula (1):

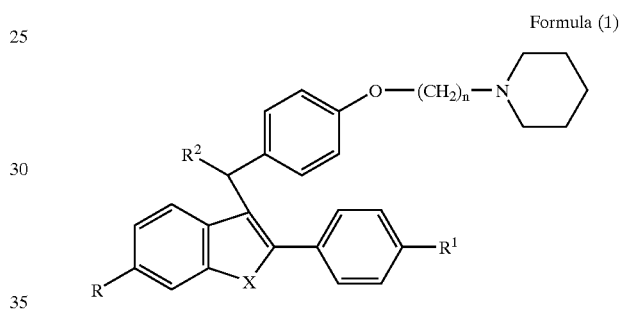

Formula (1)

wherein

R is —OH,

R$^1$ is —OH,

R$^2$ is —H, n is 2 or 3 and

X is sulfur, or a pharmaceutically acceptable salt thereof.

2. A pharmaceutical composition comprising the compound or salt of claim 1.

3. A method of treating bone loss, breast cancer or prostate cancer comprising administering an effective amount of the compound of claim 1.